(12) United States Patent
Verderio et al.

(10) Patent No.: US 8,999,655 B2
(45) Date of Patent: Apr. 7, 2015

(54) INCREASE OF MYELOID MICROVESICLES IN THE CEREBROSPINAL FLUID AS BIOMARKER OF MICROGLIA/MACROPHAGE ACTIVATION IN NEUROLOGICAL DISORDERS

(75) Inventors: Claudia Verderio, Rome (IT); Michela Matteoli, Milan (IT); Roberto Furlan, Milan (IT)

(73) Assignees: Consiglio Nazionale delle Ricerche, Rome (IT); Universita degli Studi di Milano, Milan (IT); Ospedale San Raffaele S.r.l., Milan (IT)

( * ) Notice: Subject to any disclaimer, the term of this patent is extended or adjusted under 35 U.S.C. 154(b) by 0 days.

(21) Appl. No.: 13/581,646

(22) PCT Filed: Mar. 3, 2011

(86) PCT No.: PCT/IB2011/050915
§ 371 (c)(1),
(2), (4) Date: Aug. 29, 2012

(87) PCT Pub. No.: WO2011/107962
PCT Pub. Date: Sep. 9, 2011

(65) Prior Publication Data
US 2013/0040318 A1     Feb. 14, 2013

Related U.S. Application Data

(60) Provisional application No. 61/310,048, filed on Mar. 3, 2010.

(51) Int. Cl.
*G01N 33/50* (2006.01)
*G01N 33/566* (2006.01)
*G01N 33/68* (2006.01)
*G01N 33/98* (2006.01)
(Continued)

(52) U.S. Cl.
CPC ........ *G01N 33/6896* (2013.01); *G01N 33/5076* (2013.01); *G01N 33/5091* (2013.01); *G01N 2800/28* (2013.01); *G01N 2800/52* (2013.01); *G01N 2800/56* (2013.01)

(58) Field of Classification Search
None
See application file for complete search history.

(56) References Cited

U.S. PATENT DOCUMENTS

2012/0178177 A1* 7/2012 Delerive et al. ............... 436/172

FOREIGN PATENT DOCUMENTS

| WO | 03/069347 A2 | 8/2003 |
|---|---|---|
| WO | 2011/018710 A2 | 2/2011 |

OTHER PUBLICATIONS

Horstman et al., Cell-derived microparticles and exosomes in neuro inflammatory disorders. International review of Neurobiology vol. 79 (2007) 227-268.*

(Continued)

*Primary Examiner* — Gregory S Emch
*Assistant Examiner* — Aurora M Fontainhas
(74) *Attorney, Agent, or Firm* — Lucas & Mercanti, LLP

(57) ABSTRACT

The present invention relates to a method for the diagnostic and/or prognostic of a neurological disease characterized by an inflammation process in a subject comprising measuring the amount of myeloid derived microvesicles in a cerebrospinal fluid sample obtained from the subject. The invention further relates to a method for predicting and/or monitoring the efficacy of a treatment for a neurological pathology or for monitoring a neurological disease progression.

12 Claims, 17 Drawing Sheets

(51) Int. Cl.
G01N 23/22 (2006.01)
C12Q 1/68 (2006.01)

(56) References Cited

OTHER PUBLICATIONS

Scolding et al., Vesicular removal by oligodendrocytes of membrane attack complexes formed by activated complement. Nature vol. 339, Jun. 1989, 620-622.*

Bianco et al., Astrocyte-Derived ATP Induces Vesicle Shedding and IL-1 beta Release from Microglia. J Immunol 2005; 174:7268-7277.*

Craner et al., Sodium Channels Contribute to Microglia/Macrophage Activation and Function in EAE and MS. GLIA 49:220-229 (2005).*

Doeuvre, Loic, et al: "Cell-derived microparticles: a new challenege in neuroscience", Journal of Neurochemistry, Jul. 2009, vol. 110, No. 2, Jul. 2009, pp. 457-468.

Matsuka, et al: "Two types of neurotransmitter release patterns in isolectin B4-positive and negative trigeminal ganglion neurons", Neuroscience, New York, NY, US, vol. 144, No. 2, Dec. 7, 2006, pp. 665-674.

Verderio, Claudia, et al: "Increase of myeloid microvesicles in the cerebrospinal fluid as biomarker of microglia/macrophage activation in neuroinflammatory disorders", Purinergic Signalling, vol. 6, no. Suppl. 1, Jun. 2010, pp. 90-91.

* cited by examiner

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: synthetic primer

<400> SEQUENCE: 1
caggaaggca gtgtcactca                                            20

<210> SEQ ID NO 2
<211> LENGTH: 20
<212> TYPE: DNA
<213> ORGANISM: Artificial Sequence
<220> FEATURE:
<223> OTHER INFORMATION: synthetic primer

<400> SEQUENCE: 2
gggattttgt cgttgcttgt                                            20

<210> SEQ ID NO 3
<211> LENGTH: 20
<212> TYPE: DNA
<213> ORGANISM: Artificial Sequence
<220> FEATURE:
<223> OTHER INFORMATION: synthetic primer

<400> SEQUENCE: 3
ccggagagga gacttcacag                                            20

<210> SEQ ID NO 4
<211> LENGTH: 20
<212> TYPE: DNA
<213> ORGANISM: Artificial Sequence
<220> FEATURE:
<223> OTHER INFORMATION: synthetic primer

<400> SEQUENCE: 4
tggtccttag ccactccttc                                            20

<210> SEQ ID NO 5
<211> LENGTH: 20
<212> TYPE: DNA
<213> ORGANISM: Artificial Sequence
<220> FEATURE:
<223> OTHER INFORMATION: synthetic primer
```

<400> SEQUENCE: 5
aagtccagcc gcaccaccct                                                    20

<210> SEQ ID NO 6
<211> LENGTH: 20
<212> TYPE: DNA
<213> ORGANISM: Artificial Sequence
<220> FEATURE:
<223> OTHER INFORMATION: synthetic primer

<400> SEQUENCE: 6
tgcagacgcc atggtgcagg                                                    20

<210> SEQ ID NO 7
<211> LENGTH: 20
<212> TYPE: DNA
<213> ORGANISM: Artificial Sequence
<220> FEATURE:
<223> OTHER INFORMATION: synthetic primer

<400> SEQUENCE: 7
acctggcaag tatccacagc                                                    20

<210> SEQ ID NO 8
<211> LENGTH: 20
<212> TYPE: DNA
<213> ORGANISM: Artificial Sequence
<220> FEATURE:
<223> OTHER INFORMATION: synthetic primer

<400> SEQUENCE: 8
ttttcaggcc tcaatccaac                                                    20

<210> SEQ ID NO 9
<211> LENGTH: 20
<212> TYPE: DNA
<213> ORGANISM: Artificial Sequence
<220> FEATURE:
<223> OTHER INFORMATION: synthetic primer

<400> SEQUENCE: 9
gagcacctgc ggttcgctgt                                                    20

<210> SEQ ID NO 10
<211> LENGTH: 20
<212> TYPE: DNA
<213> ORGANISM: Artificial Sequence
<220> FEATURE:
<223> OTHER INFORMATION: synthetic primer

<400> SEQUENCE: 10
gcagcagcgg atgccagtga                                                    20

<210> SEQ ID NO 11
<211> LENGTH: 29
<212> TYPE: DNA
<213> ORGANISM: Artificial Sequence
<220> FEATURE:
<223> OTHER INFORMATION: synthetic primer

<400> SEQUENCE: 11
ctagaagcat tgcggtggac gatggaggg                                          29

<210> SEQ ID NO 12
<211> LENGTH: 30

-continued

```
<212> TYPE: DNA
<213> ORGANISM: Artificial Sequence
<220> FEATURE:
<223> OTHER INFORMATION: synthetic primer

<400> SEQUENCE: 12
tgacggggtc acccacactg tgcccatcta                                30
```

INCREASE OF MYELOID MICROVESICLES IN THE CEREBROSPINAL FLUID AS BIOMARKER OF MICROGLIA/MACROPHAGE ACTIVATION IN NEUROLOGICAL DISORDERS

CROSS-REFERENCE TO RELATED APPLICATION

This application is a 371 of PCT/IB2011/050915, filed Mar. 3, 2011, which claims the benefit of U.S. Provisional Application No. 61/310,048, field Mar. 3, 2010, the contents of each of which are incorporated herein by reference.

TECHNICAL FIELD

The present invention relates to a method for the diagnosis and/or prognosis of a neurological disease characterized by an inflammatory process as well as a method for predicting and/or monitoring the efficacy of a treatment for a neurological pathology. The methods are based on the measurement of the amount of myeloid derived microvesicles in a cerebrospinal fluid sample.

BACKGROUND ART

Microvesicles (MVs) of different sub-cellular origin, and released by most cells, have been recently indicated as a novel way of intercellular communication (Al-Nedawi et al., 2009; Cocucci et al., 2009; Ratajczak et al., 2006). MVs include microparticles shed from the plasma membrane (shed MPs), also called ectosomes, and exosomes, secreted as a result of multivesicular bodies exocytosis. Both organelles mediate the transfer of lipids, proteins and genetic material from donor to target cells. Because of their small size some MVs can move from the site of discharge by diffusion and represent important vectors of inflammatory or pathogenic agents (Ardoin, 2008; Doeuvre, 2009; Emmanouilidou; Vella, 2007)}. MVs of hematopoietic/endothelial origin and derived from brain tumors are emerging as new biomarkers of tissue damage. The authors have recently shown that microglia, upon in vitro activation, shed MVs containing pro-inflammatory cytokines (Bianco et al., 2005a; Bianco et al., 2005b).

Multiple Sclerosis (MS) is an inflammatory demyelinating disease of the central nervous system. It is a chronic pathology, characterized, in 80-90% of cases, by an initial relapsing remitting course followed by a secondary progressive phase in which patients develop progressive neurological disorders. The pathological hallmark of MS is the presence within the CNS of inflammatory infiltrates, containing few autoreactive T cells, lymphocytes and microglia/macrophages (Prineas et al., 2001; Sriram and Rodriguez, 1997). MS brain is also characterized by elevated levels of the microglial-derived cytokine IL1β, which contributes to demyelination and progressive neuronal damage (Martin et al., 1995; Badovinac et al., 1998; Wiemann et al., 1998; Furlan et al., 1999; Hemmer et al., 2002; Pollak et al., 2003; Takahashi et al., 2003; Furlan et al., 2007).

The authors have recently shown that IL1β is contained in and released from microparticles (MPs) which are shed from the plasma membrane of microglia upon cell activation (Bianco et al., 2005; Bianco et al., 2009). Plasma membrane-derived MPs, together with exosomes—the latter secreted as a result of multivesicular bodies fusion with the plasma membrane—are extracellular microvesicles (MVs), involved in the intercellular transfer of lipid and protein components as well as of genetic materials from donor to target cells and are important vectors of inflammatory or pathogenic agents (Rajendran et al., 2006; Ratajczak et al., 2006; Vella et al., 2007; Simons and Raposo 2009; Bianco et al, 2009; Qu et al., 2009). Since microglia is known to be activated in all major steps of MS and elevated levels of IL1β are present in MS brain tissue, in the present invention it was verified whether the production of MVs from microglia, both MPs and exosomes, increases in the course of Experimental Autoimmune Encephalomyelitis (EAE), a rodent model of human MS, and contributes to neuronal damage. Indeed, although MVs deriving from blood cells, endothelial cells or tumors are emerging as new messengers/biomarkers unveiling an existing situation of damage—i.e. ischemic cerebrovascular accidents, transient ischemic attacks (Diamant et al. 2004; Morel et al. 2004b; Distler et al. 2005; Pilzer et al. 2005; Morel et al. 2006; Leroyer et al. 2008; Douvre et al. 2009; Huttner et al. 2008)—microglia-derived MVs have been only recently described and characterized in vitro (Bianco et al., 2005; Bianco et al., 2009). In particular, the possibility that these organelles may be present in vivo at concentrations varying in relation with the pathophysiological brain context has never been explored, as the few reports available on MVs in CNS pathologies have focused only on endothelial- or blood cells-derived MVs (Horstman et al., 2007).

For example, WO2009/100029 discloses a diagnostic method, for the detection of a disease or other medical conditions in a subject, by determining the concentration of microvesicles within a biological sample, in particular blood-derived urinary microvesicles.

The document WO2010/072410 describes a method for immobilizing microvesicles to a coated surface using a laminar flow as well as means and methods for detecting microvesicles and uses thereof for detecting or determining diseases related to microvesicles and related kit. In this document, microvesicles are isolated from platelet poor plasma.

There is therefore the need for a method that allows the diagnosis and/or prognosis of a neurological disorder characterized by an inflammatory process. The process and/or the disorder being preferably characterized by microglial activation. There is the need for a marker specific of microglial activation. Such marker, present in the CSF, can be used for diagnostic or prognostic purposes.

In the present invention, the authors investigated in great details whether the amount of myeloid MVs increase in vivo in the course of EAE, reflecting microglial activation and the development of the inflammatory plaque. Given that the cerebrospinal fluid (CSF) is in direct contact with brain cells, the authors tested the possibility that CSF may be a direct recipient of microglia shedding products. Quantitative analysis of microglia-derived MVs in the CSF of EAE mice indicated a strict association between levels of microglia-derived MVs and disease course. The present results identify microglial MVs as strong biomarkers for diagnosis and monitoring of MS, thus revealing that CSF has a greater potential than previously thought for diagnosis of neuro-inflammatory diseases.

The authors demonstrate in the present invention that the number of microglia/macrophages-derived MVs is significantly increased in the cerebrospinal fluid (CSF) of rodents and humans during diseases characterized by microglial activation. During multiple sclerosis, an autoimmune disease in which T cells reactive to myelin initiate an inflammatory response in the brain, MVs derived from microglia/macrophages deliver a pro-inflammatory signal to neighbouring cells and contribute to neuroinflammation. Thus, these findings demonstrate a previously unappreciated role for microglia/ macrophage MVs in neuroinflammatory diseases and identify MVs as a novel biomarker of brain inflammation.

Whereas very few reports described the detection of platelet-, endothelial cell- and oligodendrocyte-derived MVs in the CSF during disease (Doeuvre et al., 2009; Scolding et al., 1989), the presence of MVs of microglia/macrophage origin has never been reported.

SUMMARY OF THE INVENTION

Cerebrospinal fluid (CSF) represents an easily accessible source of material for diagnosis and monitoring of neurological diseases. As a direct recipient of cell shedding products, it is a potential indicator of abnormal CNS states such as inflammation, infection, neurodegenerative processes and tumor growth (Zougman, 2008). In the present invention, the authors show that rodent and human CSF contains microvesicles of microglial origin, distinct from apoptotic bodies, similar in size and content to microvesicles released in vitro from microglia exposed to ATP, a mediator of intercellular communication and a danger signal (Bianco et al., 2005; 2009). Of note, levels of microglia-derived microvesicles increase in rodent CSF upon inflammation induced by intracerebral injection of lentiviral vectors codifying for IFNγ or TNFα, a protocol known to induce dramatic activation of microglia/macrophages (FIG. 4). These results represent the proof of principle that the amount of microglial MVs in the CSF reflects the activation state of microglia in vivo and thus, the extent of the inflammatory condition. In line with these results, microglia-derived microvesicles also increase in rodent CSF in the course of Experimental Autoimmune Encephalomyelitis (EAE), a model for Multiple Sclerosis, reflecting disease activity. In both chronic and relapsing EAE, the number of microglia-derived microvesicles is closely associated to the disease course, increasing with EAE severity and decreasing with recovery. Analysis of microglial microvesicles in CSF collected from patients with clinically definite or probable Multiple Sclerosis showed elevated levels in all disease phases as compared to age- and sex-matched individuals with other neurological disorders, with the exception of Alzheimer's Disease patients. These findings link microglia activation to the propagation of microvesicles in vivo and identify CSF microparticles as a novel biomarker for diagnosis and monitoring of responsiveness to pharmacological treatments of patients affected by Multiple Sclerosis or other diseases characterized by microglia activation.

It is therefore an object of the present invention a method for the diagnosis and/or prognosis of a neurological disease characterized by an inflammation process in a subject comprising measuring the amount of myeloid derived microvesicles in a cerebrospinal fluid sample obtained from the subject, wherein if the measured amount is above a control value, the subject is affected by a neurological disease characterized by an inflammation process.

In the present invention, if the amount of myeloid derived microvesicles is above 1.5 to 2 microvesicle/μl, the subject is affected by a neurological disease characterized by an inflammation process.

Preferably, the neurological disease and/or the inflammation process is characterized and/or induced by microglial activation.

In a preferred embodiment, the neurological disease is selected from the group of Multiple sclerosis, Alzheimer's disease, clinically isolated syndrome (CIS), encephalitis, meningoencephalitis, acute disseminated encephalomyelopathy (ADEM), Guillan Barré Syndrome (GBS), neuromyelitis optica (NMO), chronic inflammatory demyelinating polyneuropathy (CIDP), inflammatory neuropathies, epilepsy.

Preferably, the myeloid derived microvesicles are positive for the isolectin B4.

Still preferably, the myeloid derived microvesicles are further positive for a marker selected from: isolectin ba-1, OX42 or CD11b.

In a preferred embodiment, the amount of the myeloid derived microvesicles is measured by means of flow cytometry technology.

In a preferred embodiment, the amount of the myeloid derived microvesicles is measured by means of immunogold electron microscopy.

Preferably, the control value is between 1.5 to 2 microvesicles/μl.

It is a further object of the invention, a method for predicting and/or monitoring the efficacy of a treatment for a neurological disease or for monitoring a neurological disease progression in a subject comprising:
measuring the amount of myeloid derived microvesicles in a cerebrospinal fluid sample obtained from the subject,
comparing the measured amount to a control value.

Preferably, the neurological disease is characterized and/or induced by an inflammation process.

Still preferably, the neurological disease and/or the inflammation process is characterized and/or induced by microglial activation.

In a preferred embodiment, the neurological disease is selected from the group of Multiple sclerosis, Alzheimer's disease, clinically isolated syndrome (CIS), encephalitis, meningoencephalitis, acute disseminated encephalomyelopathy (ADEM), Guillan Barré Syndrome (GBS), neuromyelitis optica (NMO), chronic inflammatory demyelinating polyneuropathy (CIDP), inflammatory neuropathies, epilepsy.

In a still preferred embodiment, the myeloid derived microvesicles are positive for the isolectin B4.

Preferably, the myeloid derived microvesicles are further positive for a marker selected from: isolectin ba-1, OX42.

Still preferably, the amount of the myeloid derived microvesicles is measured by means of flow cytometry technology.

Still preferably, the amount of the myeloid derived microvesicles is measured by means of immunogold electron microscopy.

In the present invention, myeloid-derived microvesicles are circular membrane fragments, ranging in size from 50 nm to 1 μm in diameter, and positive for myeloid markers, such as for example Ib4, Iba-1, CD11b, on their surface. Microvesicles are circular membrane fragments, ranging in size from 50 nm to 1 μm in diameter of different subcellular origin released by most known eukaryotic cell types.

In the present invention, the control value may also be selected from a value measured in a healthy patient, a patient affected by a non-neurological pathology, a patient affected by a neurological pathology not characterized by an inflammation process, a patient affected by a neurological disease characterized by an inflammation process before a therapeutic treatment, a patient affected by a neurological disease characterized by an inflammation process during the time course of a therapeutic treatment, a patient affected by a neurological disease characterized by an inflammation process at various time point during the course of the disease.

BRIEF DESCRIPTION OF THE DRAWINGS

The invention will be described by means of non-limiting examples in references to the following figures.

DETAILED DESCRIPTION OF THE INVENTION

Materials and Methods
Isolation of CSF MVs

Figure 9:
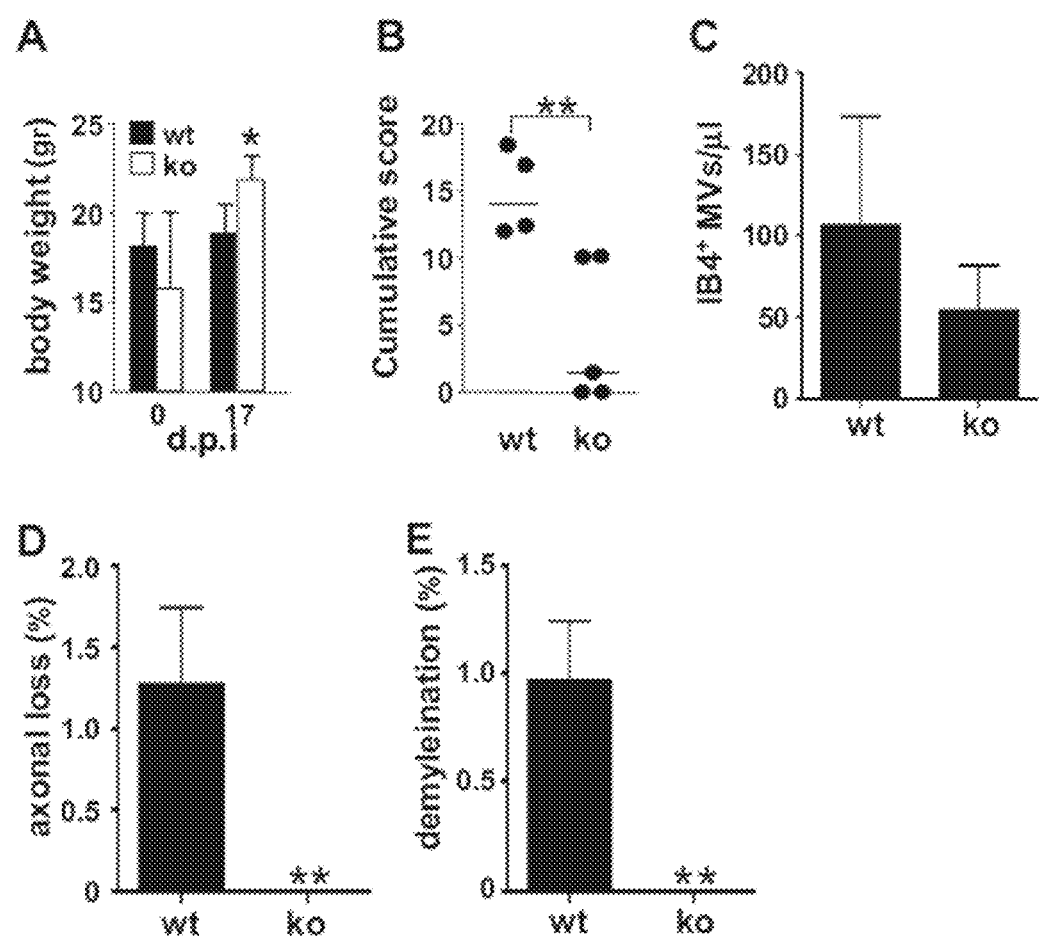
FIG. 9. EAE is inhibited in A-SMase knock out mice A-B. Graphs represent mean body weight, a measure of wealthness, (A) and disease burden, evaluated as cumulative clinical score (B), of wild type and A-SMase$^{-/-}$ mice. Both clinical parameters show that disease is clearly less severe in A-SMase$^{-/-}$ mice. d.p.i.=days post-immunization C. Flow cytometry analysis of $IB4^+$ microglia/macrophage-derived MVs in the CSF of EAE wild type and A-SMase$^{-/-}$ mice 17 days after immunization. CSF MVs detected in A-SMase$^{-/-}$ mice may be mainly exosomes, that are not A-SMase-dependent. D-E. A-SMase$^{-/-}$ EAE mice appear completely protected from CNS tissue damage as evaluated by axonal loss (D), and demyelination (E). wt=wild type, ko=A-SMase$^{-/-}$ mice. *$p<0.05$; **$p<0.01$.

To collect CSF, rats or mice have been anaesthetized by intraperitoneal injection of 4% Chloral solution and CSF has been sampled from the cisterna magna using a glass capillary (about 10 µl/mouse; about 100 µl/rat) and checked for the absence of blood contamination. CSF pooled from 2-5 rats has been diluted with 0.5-1 ml ice-cold PBS containing protease inhibitors and subjected to differential centrifugation to obtain three vesicles pellets, P2, P3 and P4 pellets, as previously described (Bianco et al., 2009). The resulting pellets were either re-suspended in SDS sample buffer for western blotting, or re-suspended (and fixed when needed) for negative staining electron microscopy or fluorescence microscopy.
Electron Microscopy Negative Staining and Immunogold P2, P3 and P4 MVs or apoptotic bodies from UV irradiated N9 microglial cells were fixed with 4% paraphormaldeyde and adsorbed to 400-mesh formvar/carbon-coated grids; grids with adherent MVs were then negative contrasted with 1% uranyl acetate and analysed with Philips CM10 transmission electron microscope in bright field. At least 50 vesicles from three different preparations were analyzed from each pellet. Immunogold labeling for CD11b/c (OX42, Harlan Sera-Lab, UK) was performed on pelleted MVs, fixed and adsorbed to 400-mesh formvar/carbon-coated grids, incubated with monoclonal mouse anti-rat Ab against CD11b/c for 1 h, followed by 12-nm gold coupled secondary goat anti-mouse antibody (Jackson ImmunoResearch Laboratories). MVs were then treated with 1% gluthaldheyde for 20' and finally subjected to negative staining using 1% uranyl acetate for 5 min at RT. MVs from primary rat microglia were used as positive control, whereas synaptic vesicles from rat crude synaptome preparation were used as negative controls.
Fluorescence Microscopy of CSF MVs MVs pelletted from rat CSF at 110,000 g for 1 h were re-suspended in about 20 µl of PBS buffer, stained with Annexin-V-FITC, CD11b-PE or IB4-FITC, which all bind extracellular components, spotted on glass microscope slides, covered with glass coverslips, sealed and observed with an inverted Zeiss Axiovert 200M microscope. Staining of fixed MVs with Abs directed against intracellular epitopes, i.e. GFAP, MBP, IBA-1 and SNAP-25, was performed as follows: primary antibodies was added in a 1:1 volume of PBS buffer containing goat serum and 0.3% TritonX-100 and incubations were allowed for 1 h at RT. Primary Ab-conjugated MVs were then washed with PBS and pelletted before incubation with fluorochrome-conjugated secondary Abs for 2 h at RT and further washing in PBS. Re-pelletted labelled vesicles were then spotted on glass microscope slides and observed at fluorescence microscope. CSF collected from CX3CR1-EGFP mice was directly stained for Cd11b, spotted on glass microscope, sealed and observed with an inverted Zeiss Axiovert 200M microscope to analyzed the presence of EGFP-labelled MVs.
Western Blotting of CSF MVs P2, P3 and P4 CSF MVs obtained by differential centrifugation from 200-500 µl of rat CSF were re-suspended in SDS sample buffer, loaded on a single lane of a 12% polyacrylamide gel and blotted onto nitrocellulose filters. 0.2 µg of corpus callosum homogenate, 10 µg of rat brain and 1 µg of cortical astrocytes lysate were run in the same gel, as positive controls. Selected proteins were detected with specific Abs followed by HRP-conjugated secondary Abs and revealed using an ECL system.
Flow Cytometry Analysis of Myeloid CSF MVs CSF collected from naïve mice or mice exposed to different inflammatory treatments was directly stained with FITC-conjugate Isolectin B4 from *Baindeiraea Simplicifolia*, (IB4-FITC, SIGMA), and the phosphatydil serine ligand annexin-V in 1% BSA. Specificity of IB4 labelling was evaluated by treating IB4-FITC with 1 M melibiose (6-O-a-D-galactopyranosyl-D-glucose, Sigma M5500) for 30 min before addition to Shed MVs (FIG. 9) as previously described (Ayoub A E et al.). CSF was then diluted in PBS buffer and labelled MVs were acquired within a fixed time interval on a Canto II HTS flow cytometer (Becton Dickinson). Data were analysed using FCS 3 software (Becton Dickinson, Franklin Lakes, N.J., USA). A gate was established on size using beads of 0.5-2 µm. Whithin this gate IB4/annexin-V double positive events (number of events/µl) were evaluated as a parameter of MVs concentration in the CSF. Samples of human CSF collected from lumbar puncture (200-300 µl) were stained with IB4-FITC, annexin V-APC and CD63-PE. IB4 and annexin-V double positive events were evaluated as a parameter of shed MVs concentration while IB4 and CD63 double positive events was evaluated as a parameter of exosome concentration. The local ethical Committee has approved the study and written informed consent from all subjects was obtained.
Glial Cells Cultures and In Vitro Stimulation Primary cortical astrocytic cultures and purified microglial cultures from E21 embryonic rat pups, were obtained and maintained as previously described (Calegari et al., 1999); (Bianco et al., 2005a). Murine BV2 microglial cells, originally developed by Blasi et al. (1988) were provided by Dr. F. Aloisi (Department of Cell Biology and Neuroscience, Istituto Superiore di Sanità, Rome, Italy). Murine N9 microglia cells, established by Prof. Castagnoli, were grown as described (Bianco et al., 2005). Purified cultures of astrocytes, microglial cells or mixed glial cultures were exposed to LPS (0.4 µg/ml) or Th1 cytokines (100 U/ml IL1-β, 200 U/ml TNFα and 500 U/ml IFNγ) for 24 hours or exposed for different time points (24 h, 48 h, 72 h) to MVs (P2 and P3 fractions), pelletted from the supernatants of LPS/Th1-primed microglia stimulated with BzATP for 30 min. Recipient glial cells were incubated with an amount of shed MVs produced by a double number of microglia (about 200 MVs/per 25 mm coverslip).

At the end of incubation with different stimuli or MVs, cultured astrocytes were lysed in SDS sample buffer for western blotting or harvested with TRIZOL for RT-PCR analysis or fixed with 4% paraformaldehyde for immunocytochemistry or loaded with the calcium dye FURA-2AM for calcium imaging recordings. Purified microglia cultures exposed to shed MVs were extracted with TRIZOL for RT-PCR analysis. Microglia present in mixed glial cultures, were detached by shaking and analyzed by flow cytometry.

In a set of experiments, to evaluate possible internalization of shed MVs into recipient cells, fluorescent shed MVs, released from primary microglia pre-loaded for 1 h with the cytoplasmic fluorescent dye CellTracker green CMFDA (15 µM), were incubated for 1 h with unstained microglial cells or astrocytes. Recipient glial cells were then exposed for 3 min to IB4-Texas red at RT, before being fixed with 4% paraformaldehyde, to allow the specific staining of MVs attached to the cell surface of recipient cells but not of those internalized into the cell cytoplasm. In addition, MVs isolated from GFP-expressing N9 cells (Bianco et al., 2005), were re-suspended in the culturing medium of control N9 cells and recipient glial cells were fixed 1 hour after Shed MVs addition.

Semiquantitative Reverse Transcriptase-Coupled PCR

Total RNA was isolated from rat primary astrocytes/microglia using miRNeasy Qiagen kit following the manufacturer's protocol. To remove any contaminating genomic DNA, total RNA was digested with DNase. Reverse transcriptase was performed using SuperScript® III First-Strand Synthesis System (Invitrogen) and oligo (dT)20 as primer. The resulting cDNA was amplified using FastStart Taq DNA Polymerase (Roche) and the following primers for rat pro-inflammatory genes IL-1β (339 bp), sense, 5'-CAG GAA GGC AGT GTC ACT CA-3'(SEQ ID No. 1); antisense, 5'-GGG ATT TTG TCG TTG CTT GT-3'(SEQ ID No. 2); IL-6 (473 bp), sense, 5'-CCG GAG AGG AGA CTT CAC AG-3'(SEQ ID No. 3); antisense, 5'-TGG TCC TTA GCC ACT CCT TC-3'(SEQ ID No. 4); iNOS (595 bp), sense, 5'-AAG TCC AGC CGC ACC ACC CT-3'(SEQ ID No. 5); antisense, 5'-TGC AGA CGC CAT GGT GCA GG-3'(SEQ ID No. 6); CD206 (493 pb) sense, 5'-ACC TGG CAA GTA TCC ACA GC-3'(SEQ ID No. 7); antisense, 5'-TTT TCA GGC CTC AAT CCA AC-3'(SEQ ID No. 8); COX-2 (334), sense, 5'-GAG CAC CTG CGG TTC GCT GT-3'(SEQ ID No. 9); antisense, 5'-GCA GCA GCG GAT GCC AGT GA-3'(SEQ ID No. 10). Amplified products were electrophoresed on a 2% agarose gels and visualized by SYBR® safe staining. Actin (sense, 5'-CTA GAA GCA TTG CGG TGG ACG ATG GAG GG-3'(SEQ ID No. 11); antisense, 5'-TGA CGG GGT CAC CCA CAC TGT GCC CAT CTA-3'(SEQ ID No. 12)) was used to ascertain that an equivalent amount of cDNA was synthesized from different samples.

Quantitative Real-Time PCR Analysis cDNA synthesis from total RNA from rat primary astrocytes/microglia was performed using ThermoScript™ RT-PCR system (Invitrogen) and Random Hexamers as primer. IL1-β, IL-6 and iNOS mRNA levels were measured by real time PCR using Taqman® Gene Expression Assays (Rn00580432_m1*, Rn99999011_m1, Rn00561646_m1*, respectively) on the ABI-Prism7500 sequence detection system (Applied Biosystems). The mRNA expression was normalized to the label of GAPDH mRNA (Mm99999915_g1*).

Cell Fluorescence Analysis

Surface stainings for CD11b-PE, CD86-PE and IB4-Texas red were carried out for 20 min at 4° C. or 3 min at RT, before fixing the cells, plated on glass coverslips. Iba-1, GFAP and phalloidin staining was performed on cells fixed with 4% paraphormaldeyde. Nuclei were stained with 4'-6-diamidino-2-phenylindole (DAPI). Cells were mounted and observed with a Leica SP5 confocal microscope.

Flow Cytometry Analysis for Cells

After shaking, microglia cells were exposed to anti CD86-PE antibodies for 30 min a 4° C. in the presence of 1% BSA, washed with PBS, resuspended and analyzed by flow cytometry as described above. At least $5\times10^4$ events/sample were analysed.

Determination of the $[Ca^{2+}]_i$

Astrocytes cultured for 2 weeks on 25-mm-diameter coverslips were exposed to shed MVs for 72 h, loaded with 10 μM Fura-2AM for 45 min at 37° C. in the culture medium and washed in Kreb's Ringer before measuring $[Ca^{2+}]_i$ as reported previously (Grumelli et al., cell calcium). Polychrome IV (TILL Photonics, Grafelfing, Germany) was used as a light source. Fura-2 fluorescence images were collected with a PCO SuperVGA SensiCam (Axon Instruments, Forest City, Calif., USA) and analyzed with TILLvision software. After excitation at 340 and 380 nm wavelengths, the emitted light was acquired at 505 nm at 1-4 Hz. The ratio values in discrete areas of interest were calculated from sequences of images to obtain temporal analyses. Calcium concentrations were expressed as F340/380 fluorescence ratios.

Quantification of Shed MVs

Spectrophotometric quantification of $NBD-C_6-HPC$-labelled shed MVs released from primary microglia was performed in Kreb's Ringer as described previously (Bianco et al., 2009). After overnight pre-treatment with LPS (0.4 μg/ml) or Th1 cytokines (100 U/ml IL1-β, 200 U/ml TNFα and 500 U/ml IFNγ) in the presence or in the absence of minocycline (50 μg/ml), cells were incubated with 50 μM $NBD-C_6-HPC$, washed and stimulated with 100 μM BzATP. Supernatants were collected, centrifuged 10 min 300 g 4° C. to remove cells and debris, and then total fluorescence was assayed at 485/535 nm with a spectrophotometric system (1420 Multilabel Counter Victor 2—Wallac, Finland).

Western Blotting

10 μg of astrocyte lysate were loaded per lane on a 12% polyacrylamide gel and blotted onto nitrocellulose filters. Proteins were detected with specific Abs followed by HRP-conjugated secondary Abs and revealed using an ECL system. Optical density of immuno labelled, bands was measured with Image J software vers. 1.35i, and average values and SE were calculated over three independent experiments.

Lentivirus Injections for In Vivo Studies

Mice (n=5 per group) were anesthetized with 2,2,2-tribromoethanol (10 mg/ml; ½₇ of body weight) and the head was placed in a stereotactic injection apparatus (David Kopf Instruments, Tujunga, Calif., USA). Vesicular stomatitis virus-pseudotyped lentivirus (LV) LV-PGK-IFNγ and LV-PGK-TNFα, previously described in Muzio et al. (2010) were injected within the right lateral ventricle at the following coordinates: A. +0; L. +0.8 and D. −2.4.

Relapsing-Remitting and Chronic Rodent EAE

Chronic-progressive EAE was induced in C57/BL6 female mice by immunization with 200 μg/mouse of MOG35-55 derived peptide as described previously (Furlan et al., 2009). Antigens were emulsified 1:1 in complete Freund adjuvant (containing IFA plus 4 mg/ml *Mycobacterium Tuberculosis*; strain H37) and 300 μl of the final emulsion was administered at the base of the tail (100 μl) and in each flank (100 μl per site) to each mouse. Pertussis toxin (500 ng/mouse) was given twice: at the time of the first immunization and 48 hours later. The protocol to induce EAE in 6 weeks old female $A-SMase^{-/-}$ mice on SV129 background, and their littermates (kind gift of Dr. E Schuchman to AV), is identical but with reduced pertussis toxin (250 ng/mouse) in consideration of the young age the authors had to perform immunization to avoid the interference with their inherent neurological phenotype (Horinouchi et al., 1995). To obtain sub-clinical EAE for the focal MVs injections, the authors used again the same protocol as for chronic EAE, but injecting 50 μg/mouse of MOG35-55, and using 250 ng/mouse of pertussis toxin. Relapsing-remitting EAE was induced in SJL mice by two immunizations, seven days apart, with 150 mg/mouse of PLP139-151 derived peptide. Antigens were emulsified 1:1 in complete Freund adjuvant (containing IFA plus 4 mg/ml *Mycobacterium Tuberculosis*; strain H37) and 100 μl of the final emulsion were administered in one flank. Pertussis toxin (500 ng per mouse) was given twice: at the time of the first immunization and 24 hours later. CSF was collected at different time points during the disease, i.e. presymptomatic phase (10 dpi, days post injection), peak (20 dpi) and chronic phase (60 dpi) in chronic-progressive EAE model; pre-clinical phase (10 dpi), first relapse (29 dpi), first remission (35 dpi) and second relapse (48 dpi), in relapsing-remitting EAE model. Female Lewis rats weighing approx. 150 gr. were immunized under the skin of the flanks using 1 mg lyophilized spinal cord homogenate emulsified in a total of 200 µl of complete Freund adjuvant as described above.

Body weight and clinical score were recorded daily. Clinical scores were assigned according to a standard and validated 0 to 5 scale, described in Furlan et al., 2009. Cumulative disease score was calculated by adding the neurological scores recorded daily for each mouse along the whole period of observation.

All efforts were made to minimize animal suffering and to reduce the number of mice used, in accordance with the European Communities Council Directive of Nov. 24, 1986 (86/609/EEC). All procedures involving animals were performed according to the guidelines of the Institutional Animal Care and Use Committee (IACUC) of the San Raffaele Scientific Institute.

MVs Injections in EAE Mice

To evaluate formation of focal lesion upon MVs injection, mice with sub-clinical EAE (see above), 20 days post immunization, were stereotaxically injected in the corpus callosum (coordinates: 0 mm anterior, 1.0 mm lateral to the bregma and 2.2 mm in depth) with MVs (P2-P4 fractions) derived from $24 \times 10^6$ murine N9 microglial cells dissolved in a total volume of 1 µl of sterile saline.

Chemicals and Antibodies

ATP, BzATP, lipopolysaccharide (LPS), mynocycline, Fura-2/AM, FICT- and APC-annexin V, IB4-FITC, IB4-Texas red, melibiose were from Sigma-Aldrich. CellTracker green CMFDA, were from Molecular Probes, PI was BD Biosciences from $NBD-C_6$-HPC was from Invitrogen, IL1-β was from Euroclone, TNFα and IFNγ from R&D. The following antibodies were used: anti mouse CD11b-PE (BD Biosciences), anti-human CD63-PE (BD Biosciences) anti-rat CD86 (eBioscience), anti-mouse GFAP (Sigma-Aldrich), anti-human calnexin (Sigma-Aldrich), anti-mouse CNPase (Chemicon), anti-mouse MBP (Chemicon), anti-mouse SNAP-25 SMI 81 (Sternberger Monoclonals) anti-mouse Iba-1 (Wako). FTY720 was purchased from Merck Chemicals.

Neuropathological Analysis

Brain tissue sections were fixed, embedded in paraffin and stained with H&E, Luxol fast Blue, and Bielshowsky to reveal perivascular inflammatory infiltrates, demyelinated areas and axonal loss, respectively. Infiltrating microglia and T cells were stained using IB4 and anti-CD3 and revealed using a biotin-labeled secondary anti-rat antibody. Inflammatory infiltrates, demyelinated areas and axonal loss were quantified on an average of 10 complete cross-sections of spinal cord per animal. Perivascular inflammatory infiltrates, T cells, and macrophages were evaluated as the number per $mm^2$, while demyelinated areas and axonal loss were expressed as the percentage per $mm^2$.

Statistical Analysis

All data are presented as means or median±SD, from the indicated number of experiments. Data were compared using the Student's t-test for paired or unpaired data or the Mann-Whitney U-test for non-parametric data. Differences were considered to be significant if $p<0.05$ and are indicated by an asterisk; those at $p<0.01$ are indicated by double asterisks.

Patients

The authors enrolled 98 patients and controls whose CSF was sampled and analyzed for the presence of IB4+ microvesicles. The authors had 7 controls age and sex matched with patients affected by multiple sclerosis (mean age 28 years). These controls were patients undergoing knee surgery under spinal anesthesia but neurologically healthy.

The authors collected further 9 sex and age matched controls to the Alzheimer patients (mean age 64 years) that were either surgery patients undergoing spinal anesthesia, or patients with hydrocephalus, or patients with headache undergoing spinal tap for diagnostic reasons. New neurological patients were divided as follows: 21 AD patients, 5 possible AD patients, 4 patients with frontotemporal dementia (FTD), 7 patients with mild cognitive impairment (MCI), 1 patient with amiloidosis, 15 MS patients, 5 patients with clinically isolated syndrome (CIS), 2 patients with chronic inflammatory demyelinating polineuropathy (CIDP), 5 patients with poliradiculitis, 17 patients with other neurological diseases (OND). Spinal taps were immediately sent to the laboratory. Two hundred microliters are used to measure microvesicles concentration as already described by FACS. New analysis criteria were set by eliminating non-specific fluorescent signal lining at 45°. The remaining sample was subjected to differential centrifugation to eliminate cells and cell debris, and finally microvesicles were pelletted at high speed centrifugation and pellet stored in Trizol™ for RNA analysis.

Calcium Imaging Recordings

Polychrome V (TILL Photonics, Grafelfing, Germany) was used as a light source. Fura-2 fluorescence images were collected with a PCO Super VGA SensiCam (Axon Instruments, Forest City, Calif., USA) and analyzed with TILL vision software. After excitation at 340 and 380 nm wavelengths, the emitted light was acquired at 505 nm at 1-4 Hz. The ratio values in discrete areas of interest were calculated from sequences of images to obtain temporal analyses. Calcium concentrations were expressed as F340/380 fluorescence ratios.

Quantification of Neuronal Damage

Living neurons were exposed annexin-V-FITC, fixed with 4% paraphormaldeyde and counterstained with antibodies direct against the neuronal marker SNAP-25. Apoptotic processes, labelled by annexin-V, were quantified by the Image J software and normalized to SNAP-25 immunoreactivity, as an index of neurite density. Alternatively, living cells were exposed to PI, fixed and double stained for α-tubulin and Hoescht. PI positive nuclei were quantified and normalized to total Hoescht positive nuclei. α-tubulin staining was carried out to evaluate integrity of neuronal cytoskeleton. At least 10 different fields from three independent experiments have been analyzed.

Results

Figure 1:
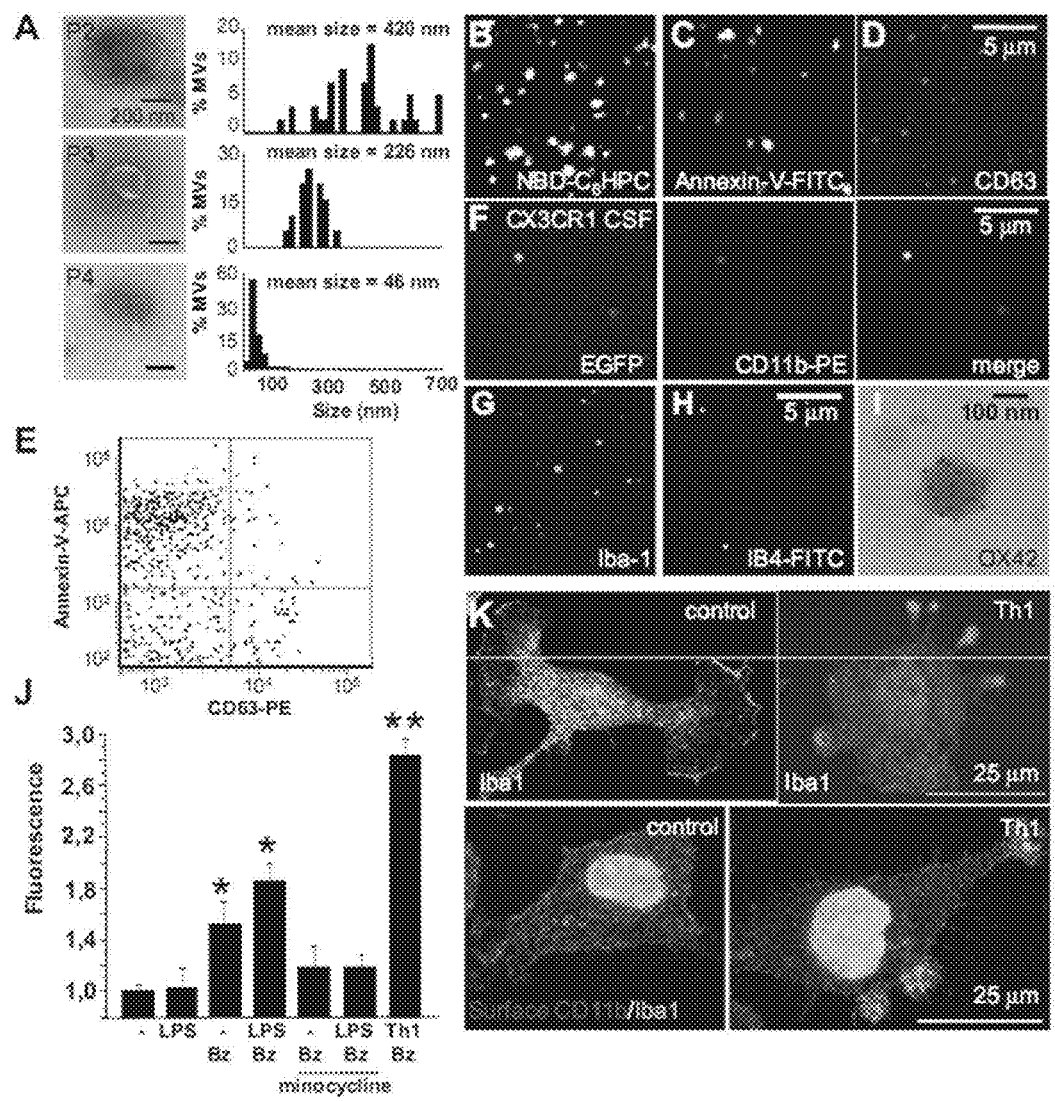
FIG. 1 Microvesicles of microglia/macrophage origin are present in the healthy CSF. A. MVs of decreasing size were isolated from the CSF of healthy rats by differential centrifugation (P2, P3, P4) and analyzed by negative staining electron microscopy (EM). MVs display a bi-layer membrane structure. Frequency histograms indicating the size distribution of MVs pelleted at increased centrifugal force are shown on the right (n=51 P2, n=73 P3, n=237 P4). B-D. CSF MVs were analyzed by fluorescence microscopy using the fluorescent phosphocholine analog NBD-$C_6$-HPC to label MV membrane (B), with the shed MPs marker phosphatidylserine, PS, using annexin-V-FITC (C), and for the exosomal marker CD63 (D). E. Flow cytometry analysis of MVs present in human CSF doubled stained for annexin-V-APC (MPs) and CD63-PE (exosomes), revealing the presence in the CSF of both exosomes and MPs shed from the plasmamembrane of myeloid cells. F. CSF MVs double fluorescent for EGFP and the microglia/macrophage marker CD11b isolated from CXCR3-EGFP transgenic mice, in which microglia/macrophages are constitutively $EGFP^+$. G-H. CSF MVs are immunopositive for the microglia/macrophage markers Iba-1 (G) or IB4-FITC (H). I. CSF MVs immunopositive for the microglia-macrophage marker OX42, analyzed by immunogold EM. J. The histogram shows the spectrophotometric analysis of fluorescent MPs shed from resting or reactive microglial cells pre-labelled with NBD-$C_6$-HPC and exposed to the $P2X_7$ agonist BzATP (100 µM) for 20 min. Treatment with the microglia inhibitor mynocicline prevented the increase in shed MPs production from microglia exposed to Th-1 cytokines or LPS for 24 h ($*p<0.05$, $**p<0.01$). K. As compared to control cells, microglia exposed to Th1 cytokines, showed accumulation of Iba-1 at blebs formed at the plasma membrane (Upper panels). Lower panels show double staining for surface CD11b and Iba-1 of control and Th1-treated BV2 murine microglial cells.
Figure 2:
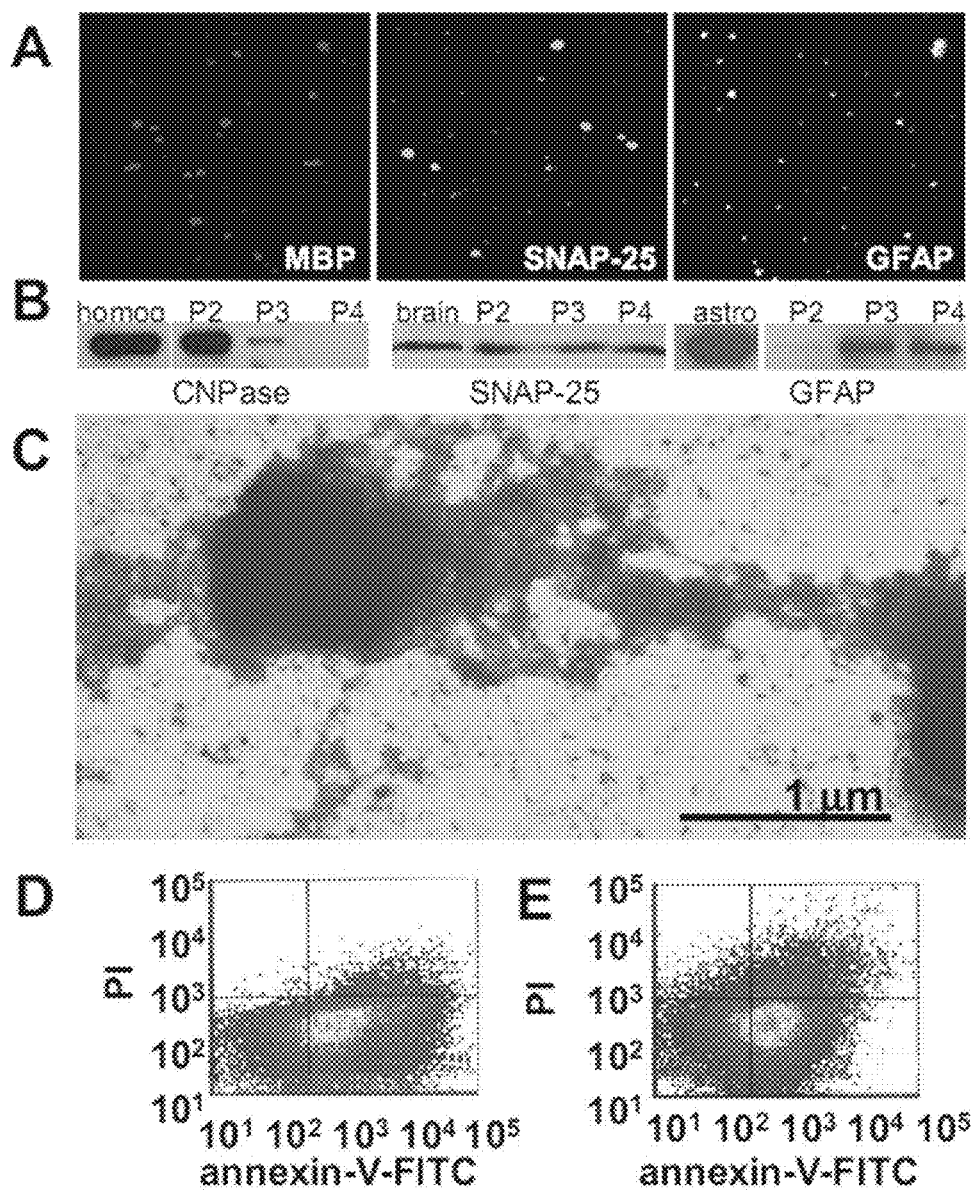
FIG. 2. MVs detected in rodent CSF are not apoptotic bodies. A. Fluorescence micrographs of MVs pelleted from rat CSF (200-500 µl) and stained for the oligodendrocyte marker MBP, the neuronal marker SNAP-25 and the astrocyte marker GFAP. B. Rat CSF MVs were separated by differential centrifugation in P2-P3 (mainly shed MVs), and P4 fractions (mainly exosomes), and assayed by WB for the oligodendrocyte marker CNPase, the neuronal marker SNAP-25 and the astrocyte marker GFAP. Homogenate of rat adult corpus callosum, rat brain and lysate of cultured astrocytes are shown as positive controls. C. Negative staining EM micrograph showing an example of apoptotic body derived from N9 microglial cells, damaged by UV. Apoptosis was induced by UV irradiation for 2 hours and apoptotic bodies present in the supernatants of damaged cells, were centrifuged 48 hours later and examined by EM. Note that apoptotic bodies appear denser and larger than CSF MVs shown in FIG. 1A. D-F. Flow cytometry analysis of MVs released from healthy N9 cells (D) or apoptotic bodies derived from UV damaged N9 cells (E) after staining with propidium iodide (PI) shows that the authors are able to detect $PI^+$ apoptotic bodies. The human CSF (F), is devoid of $PI^+$ apoptotic bodies.
Figure 3:
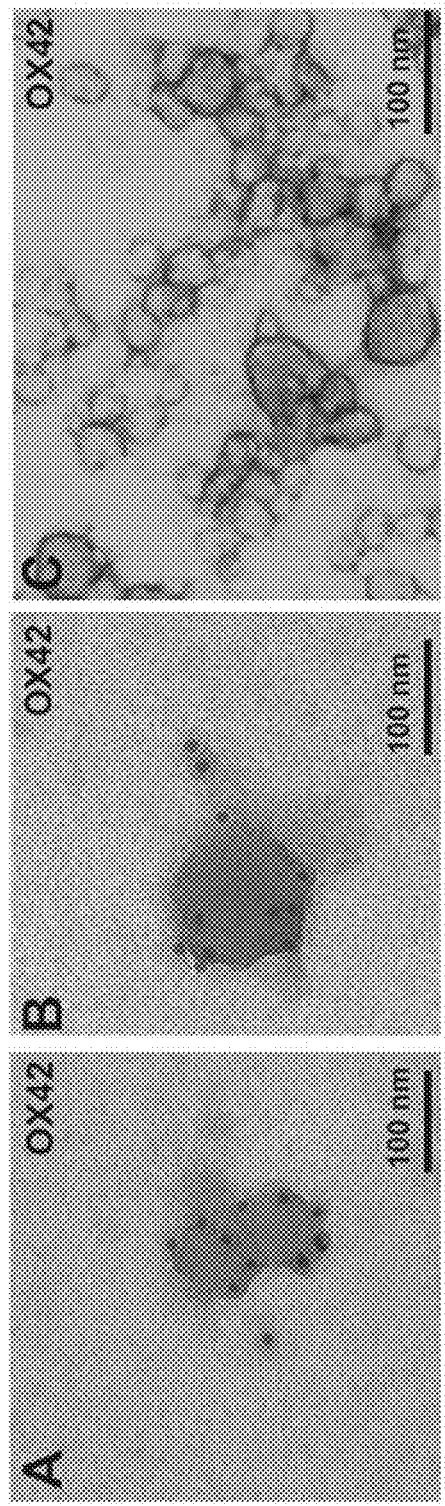
FIG. 3. Microglia/macrophage-derived MVs in rat CSF. A-C. Negative staining EM of OX42 immunogold labelled MVs present in rat CSF (A-B). A preparation of crude synaptic vesicles was used as negative control (C). About 60% of MVs present in the CSF collected from naïve rats are OX42 positive and the mean diameter of OX42 positive MVs is 112 nm.

The authors found, by negative staining electron microscopy (EM), membranous MVs, similar in size to both shed microparticles (MPs) and exosomes released from cultured glial cells, in the CSF collected from healthy rodents (FIG. 1A). Exosomes typically express tetraspan proteins such as CD63 and CD9 (Cocucci et al. 2009), while shed MPs are characterized by high levels of phosphatidyl serine (PS) (Bianco et al., 2009) on the outer membrane leaflet and bind the PS ligand annexin-V (FIG. 1B-D). By flow cytometry, the authors confirmed the presence of both annexin-V positive shed MPs and CD63 positive exosomes (FIG. 1E). The authors excluded the presence of apoptotic bodies, which are much larger and denser than MVs found in the CSF (FIG. 2A-C). Confocal microscopy and WB analysis of the CSF collected from healthy rodents revealed that MVs display either neuronal, astrocytic, oligodendroglial (FIG. 2A), or microglia/macrophage markers (Iba-1, IB4, CD11b) (FIG. 1F-H), thus indicating they can originate from different brain cells. The microglia/macrophage origin of a MVs subset was definitely confirmed by immunogold EM with antibodies to CD11b/c (OX42) (FIG. 1I and FIG. 3A-B) and by fluorescence microscopy analysis of the CSF collected from CX3CR1-EGFP transgenic mice (Jung et al. 2000) (FIG. 1F), in which microglia/macrophages express EGFP. Since blood-born macrophages are virtually absent in the healthy brain, the presence of EGFP-labelled MVs in the CSF suggests that they derive from resident microglia. Thus, the healthy CSF drains MVs from all the neural cell lineages tested, including those, like neurons and oligodendrocytes, that are strictly parenchimal and have no contact with liquoral spaces.

Figure 4:
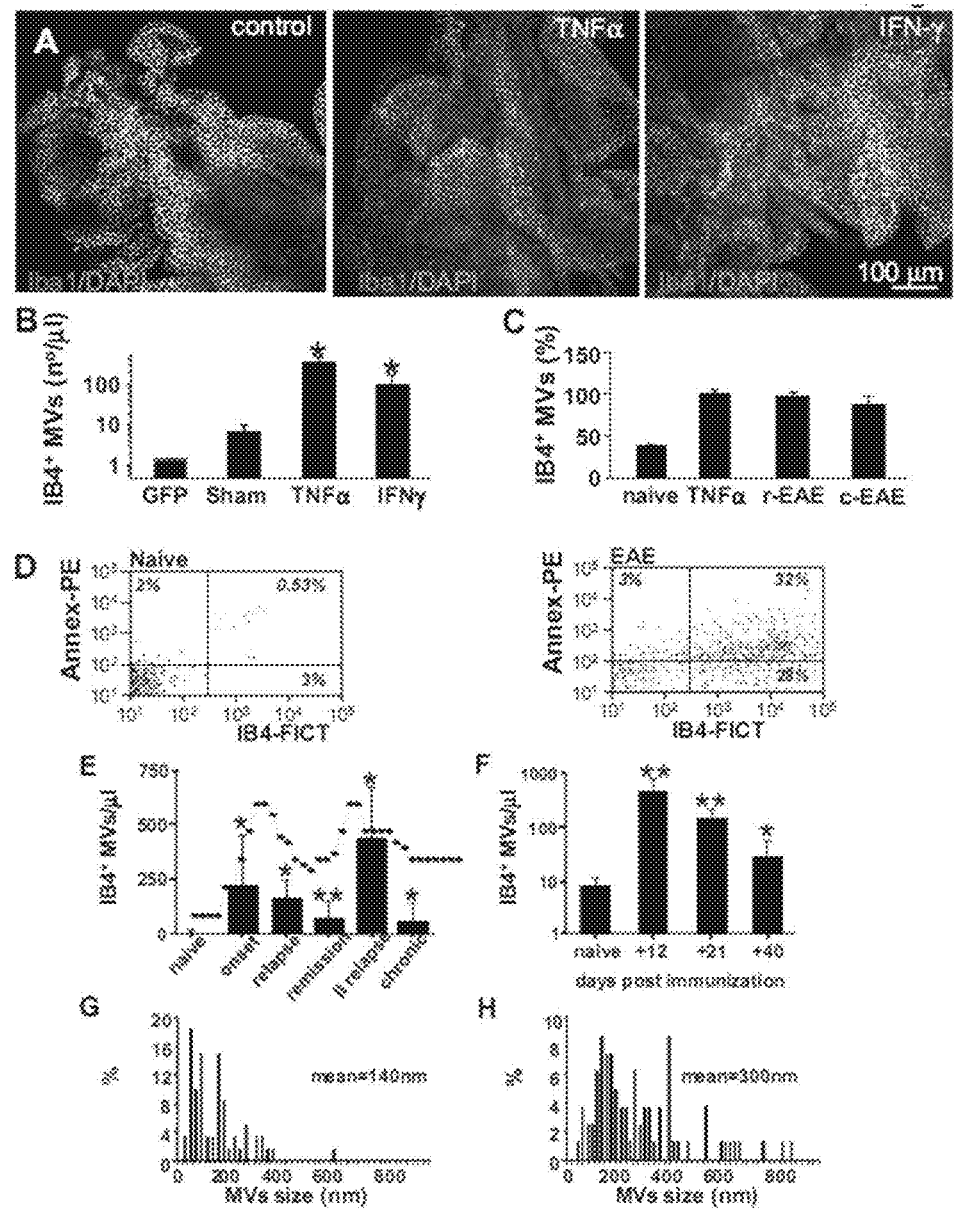
FIG. 4. The amount of microglia/macrophage-derived MVs in the CSF increases upon inflammation and reflects EAE activity. The authors collected brain tissues and CSF from naïve mice ten days after intracerebroventricular injection with lentiviral vectors codifying for GFP, IFNγ, TNFα or sham-treatment (n=5 for each condition). A. Representative choroid plexi from mice injected with a lentiviral vector codifing for GFP (control), TNFα or IFNγ, stained for the microglia/macrophage marker Iba-1(red) and DAPI to label nuclei (light blue). The number of $Iba-1^+$ cells increased in the choroid plexi of mice injected with Th1 cytokines B-C. Flow cytometry analysis using the microglia/macrophage marker IB4 shows a significant increase in the concentration of MVs in the CSF collected from Th1 cytokine-treated mice (B). Histogram in (C) shows the percentage of $IB4^+$ vs. total MVs in the CSF of naïve mice, mice injected with lentivirus codifying for TNFα, and mice affected by chronic (c-) or relapsing-remitting (r-) neuroinflammation (EAE). D. Representative flow cytometry scatter plots of $IB4^+$ and $annexin-V^+$ CSF MVs taken from a naïve or a EAE mouse, in the chronic phase of the disease. E-F. Flow cytometry analysis of $IB4^+$ CSF MVs at different disease stages during relapsing remitting (r-EAE) (E) and chronic (c-EAE) (F) EAE. CSF was collected from at least five animals at each disease stage. The clinical score of a representative mouse at different phases of r-EAE and c-EAE is superimposed onto histograms (E-F). G-H. Frequency histograms indicating the size distribution of MVs present in the CSF of healthy and EAE rats, at peak of neuroinflammation. The size of MVs (not exceeding 1 µm) rules against the apoptotic body nature of the vesicles (number of analysed MVs: 361 naive CSF; 396 EAE CSF).
Figure 5:
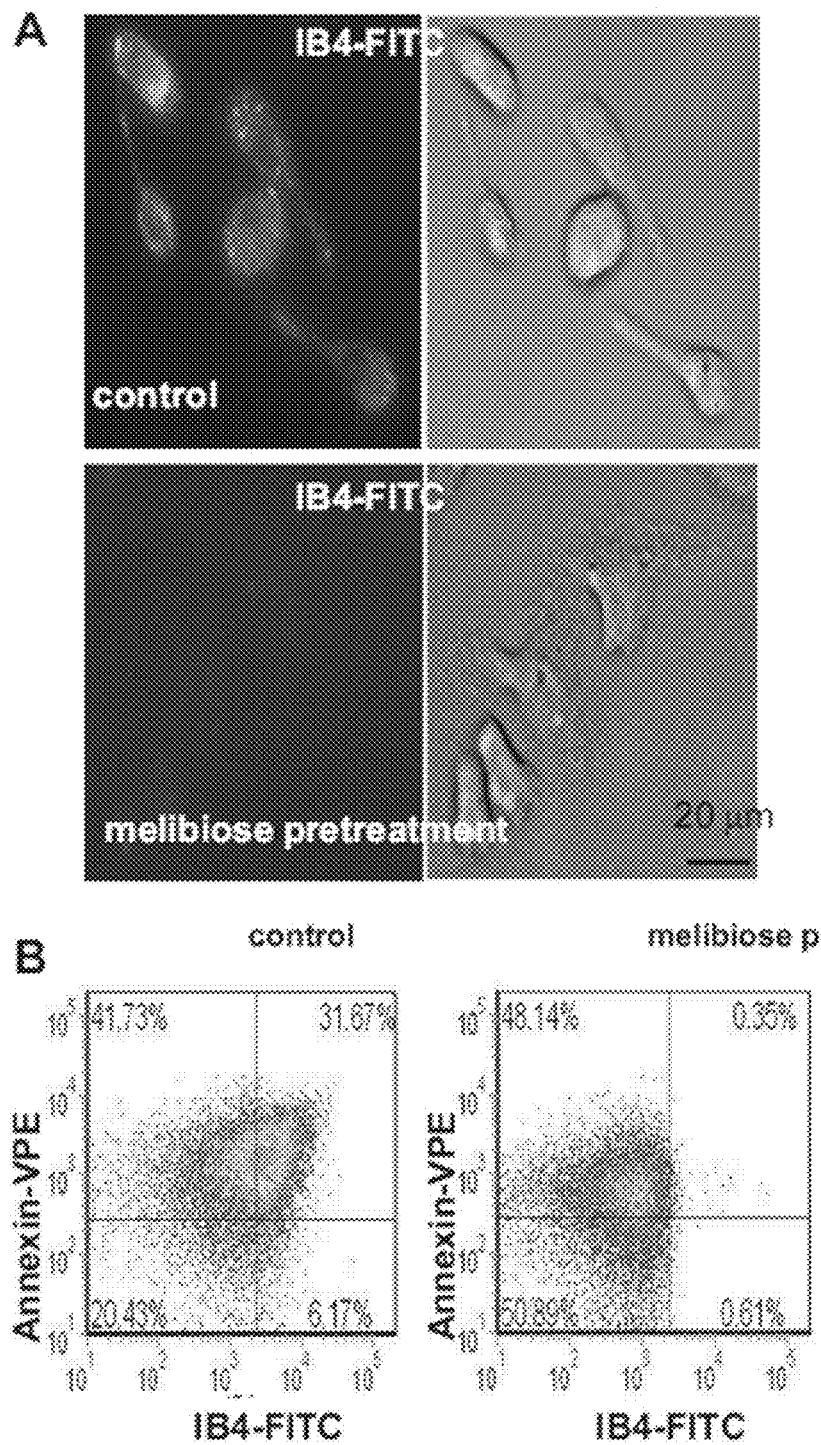
FIG. 5. IB-4 labeling of microglia/macrophage-derived MVs is specific. A. Differential interference contrast microscopy (right panels) and fluorescent images (left panels) of primary microglia labelled in vivo with IB4-FITC. Note that IB4-FITC pretreatment with 1M melibiose, a very specific ligand for the isolectin IB-4, completely prevents its binding to the cell surface, confirming specificity of the staining B. Flow cytometry analysis of intact MVs shed from N9 microglia stained with IB4-FITC. Melibiose pretreatment completely abolished IB4-FITC labeling, confirming the specificity also of the FACS assay.

The authors and others have shown that both the typical danger signal ATP and the bacterial membrane component lipopolysaccharide (LPS) enhance the release of MVs from microglia/macrophages (Bianco et al. 2009, Qu et al., 2009). The authors here show that pre-treatment with the microglia inhibitor mynocicline largely inhibits the increase in shed MPs induced by ATP in resting and LPS-primed primary microglia (FIG. 1J). In addition, the authors show that Th1 cytokines (TNF-α, INF-γ and IL1-β), which induce formation of blebs at the cell surface characterized by accumulation of Iba-1 (FIG. 1K), are the best priming stimuli to mediate shedding of MPs (FIG. 1J). All together, these data indicate that MP shedding takes place very efficiently in microglia exposed in vitro to a pro-inflammatory environment. To verify whether production of both shed MPs and exosomes from microglia/macrophages may increase during brain inflammation, the authors stereotaxically injected mice into the ventricular cavity with lentiviral vectors codifying for INF-γ or TNF-α. This treatment induces expansion of activated microglia and recruitment of macrophages from the periphery to periventricular areas of the lateral ventricles and to choroid plexi; this process typically occurs during experimental autoimmune encephalomyelitis (EAE), the animal model for multiple sclerosis (MS, Kivisakk et al., 2009) (FIG. 4A). Flow cytometry analysis demonstrated that IB4+ microglia/macrophage-derived MVs (FIG. 5) were significantly increased in the CSF of mice receiving pro-inflammatory cytokine-expressing vectors (FIG. 4B).

Microglia/macrophage-derived MVs represented the majority of total CSF MVs in TNF-α—(FIG. 4C) or IFN-γ-injected mice (not shown), while their percentage was under 50% in mice injected with the control vector. These results represent the proof of principle that the amount of microglia/macrophage-derived MVs in the CSF reflects the activation state of microglia/macrophages in vivo.

The pathological hallmark of EAE/MS is the presence within the brain of inflammatory infiltrates containing blood derived macrophages and activated microglial cells. Consistently, in mice affected by chronic (c-EAE) or relapsing EAE (r-EAE), mimicking the two most common clinical forms of MS (Hemmer et al., 2002), IB4+ MVs increased significantly, representing over 90% of total CSF MVs (FIG. 4C). The amount of microglia/macrophages MVs was closely associated to the disease course, peaking at onset and during clinical relapses, and decreasing in the chronic phase of the disease (FIG. 4E-F). Electron microscopy analysis of the CSF of EAE rats revealed that the increase of CSF MVs during neuroinflammation was not due to the presence of apoptotic bodies, but to the increase in MVs of larger size, likely shed MPs (FIG. 4G-H). Choroid plexi have been identified as the site of first entry of inflammatory cells during EAE (Kivisakk et al., 2009), and, being in direct contact with the CSF, may represent the more plausible source of MVs during neuroinflammation. However, the presence in the healthy CSF of MVs derived from neurons and oligodendrocytes (FIG. 2A), which are not in direct contact with liquoral spaces, suggests that also MVs released from parenchimal microglia can enter the CSF.

Figure 6:
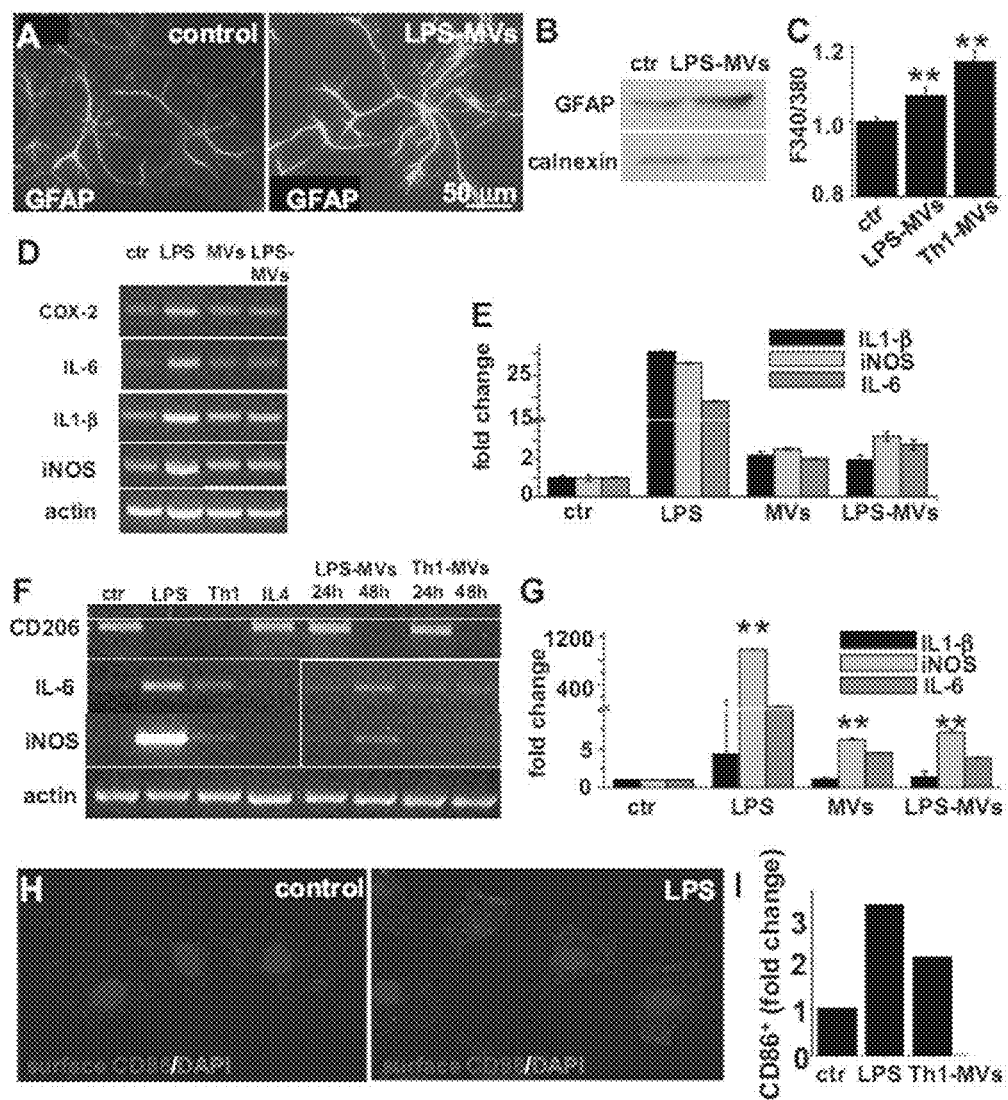
FIG. 6. MVs shed from reactive microglia deliver a pro-inflammatory signal to glial cells in vitro. A-B. As compared to control cultures, astrocytes become reactive (hypertrophic and with thicker processes) upon in vitro exposure to MVs shed from LPS-treated primary microglia (A), and display increased expression of the activation marker GFAP over the endoplasmic reticulum control protein calnexin, as shown by WB in (B). C. Astrocytes exposed to shed MVs from LPS- and Th1-treated microglia for 72 hours show increased cytoplasmic calcium concentration expressed as F340/380 fluorescence ratio. Data normalized to control represent mean values from 2 independent experiments (number of recorded cells 59, control; 41, LPS-MPs; 144, control and 139, Th1-MVs). D-E. RT-PCR for COX-2, IL-6, IL-1β, and iNOS mRNA in control astrocytes, astrocytes activated overnight with LPS and astrocytes exposed 48 hours to LPS-MVs. Data are representative of three separate experiments. Amplicons run on agarose gels, compared to actin, are shown in (D), while real time quantitative evaluation is shown in (E). Shed MVs released from primed microglia significantly increase iNOS, IL-6 and IL-β mRNA in astrocytes ($*=p<0.05$). F-G. As previously described, Th1 cytokines polarize microglia towards a pro-inflammatory M1 phenotype while Th2 cytokines towards an immuno-modulating M2 phenotype characterized by the reciprocal expression of M1 (iNOS and IL-6) or M2 (CD206) markers. Coherently, administration of shed MVs induces expression in recipient microglia of M1 and inhibition of M2 markers, evaluated, as above, both qualitatively (F) and quantitatively by real time RT-PCR (G). Data are representative of two separate experiments. H-I. Increased surface expression of the activation marker CD86 (red) in microglia exposed overnight to LPS, as compared to control. Nuclei are shown in blu with DAPI staining (I). Quantitative flow cytometry analysis of CD86 surface expression in microglia maintained in control condition, treated for 3 hours with LPS, or incubated overnight with MPs derived from Th1-primed microglial cells.
Figure 7:
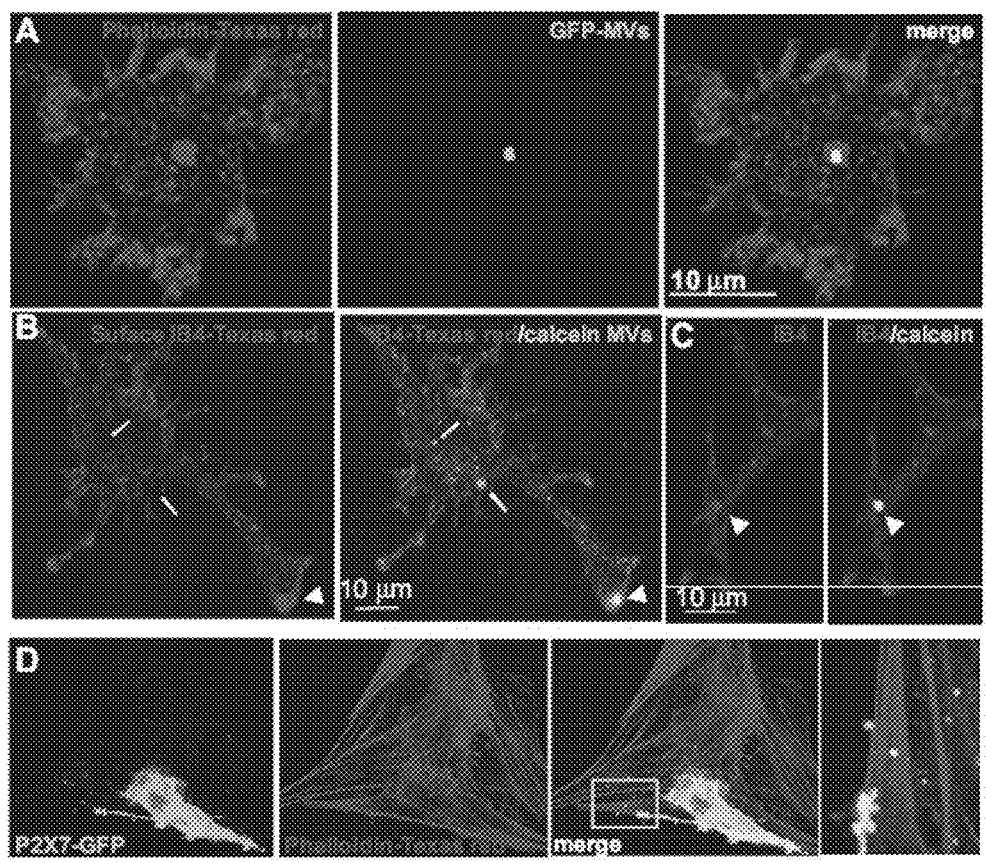
FIG. 7. MVs shed from cultured microglia are internalized by recipient glial cells. A. Confocal images of N9 cells exposed for 1 hour to GFP-labelled shed MVs isolated from the supernatant of GFP-expressing N9 cells, fixed and stained with the f-actin ligand phalloidin (in red). Note the actin ring surrounding an internalized GFP-labelled shed MV. B-C. Confocal images of primary microglia showing in red surface staining for IB-4 and in green shed MVs derived from Cell-Tracker green CMFDA (calcein) loaded primary microglia. Calcein-storing shed MVs were incubated with unstained microglia. After 1 h microglia cultures were exposed to IB-4-Texas red before being fixed. This protocol allows IB-4 staining of shed MVs attached to the cell surface of recipient microglia but not of those already internalized into the cells. Arrows in B point to calcein single positive internalized shed MVs while arrowheads in B and C point to calcein/IB-4 double positive shed MVs attached to the microglia surface. D. Confocal images of astrocyte-microglia co-cultures showing the association of $P2X_7$-GFP tagged MVs (green) with f-actin (astrocytic stress fibers), stained by phalloidin (red). $P2X_7$-GFP tagged MVs derive from microglial cells transfected with the $P2X_7$ ATP receptor fused to GFP (1 is present in the shown field). The region outlined by the inset is shown at higher magnification on the left.
Figure 13:
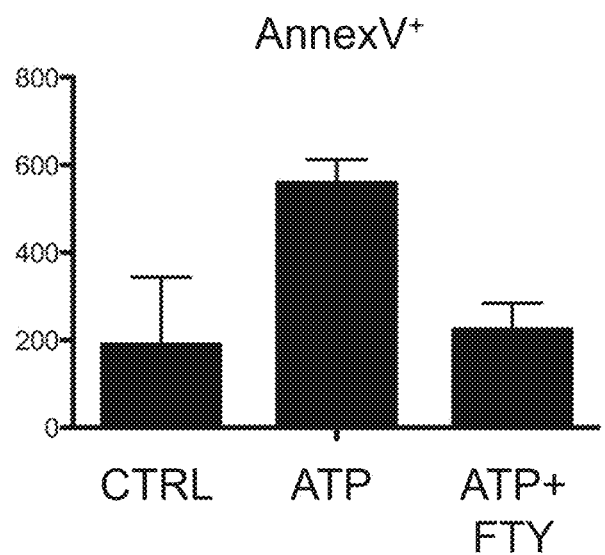
FIG. 13. FTY720 treatment. Primary mouse microglia was pre-treated, or not, with FTY720, also named fingolimod or Gylenia, currently in course of registration for the treatment of multiple sclerosis, for 30 min., then ATP was added for further 30 min. to induce the release of AnnexinV$^+$ shed vesicles, as measured by FACS. Treatment with FTY720 completely prevented the release of shed vesicles above background levels.

To define whether microglia/macrophages-derived MVs represent causative and/or amplifying agents of inflammation, primary glial cells were exposed in vitro to MPs shed from either Th1/LPS-primed or unstimulated microglia and the glial response to MPs was analyzed. Addition of MPs up-regulated astrocytes' mRNAs levels of IL1-β, IL6, iNOs, and COX-2 (FIG. 6D-E), and induced changes in cell morphology. Astrocytes appeared hypertrophic, displayed numerous thicker processes (FIG. 6A), up-regulated the expression levels of GFAP (FIG. 6B) and showed increased cytoplasmic calcium concentration (FIG. 6C). Primary microglia responded in vitro to shed MPs derived from either Th1/LPS-primed and un-stimulated microglial cells by up-regulating the T cell co-receptor ligand CD86 on the cell surface (FIG. 6H-I), suppressing the expression of the mannose receptor CD206, associated with tissue repair (Mantovani et al., 2004; Michelucci et al., 2009; Pluchino et al., 2008) (FIG. 6F), and increasing the expression of inflammatory markers such as iNOs, IL-6 and IL-1β (FIG. 6F-G). Acquisition of reactive glial phenotype was likely a consequence of internalization of shed MPs into recipient cells (FIG. 7A-C). The transfer of MVs between glial cells spontaneously occurred in cultures, as indicated by the presence of GFP+ MVs derived from GFP-P2X7-expressing microglia inside adjacent astrocytes (FIG. 7D). In addition, the authors also found that shed MPs can target neighbouring neurons, enhancing glutamatergic transmission (data not shown). Altogether, these data suggest that shed MPs by propagating a reactive phenotype to neighbouring glial cells and affecting neuronal exocytosis, may critically contribute to amplify inflammation in the CNS. To evaluate if this occurs also in vivo, the authors stereotaxically injected MVs derived from cultured microglia into the corpus callosum of mice affected by subclinical EAE. Hystological examination of EAE brain revealed numerous perivascular inflammatory foci, close to the site of MVs injection (FIG. 8A-B), which were not present in saline injected controls. These data strongly suggest that MVs play an active role in inducing CNS neuroinflammation. The authors have previously shown that MVs shedding is inhibited by acid sphingomyelinase (A-SMase) inhibitors and is abolished in glial cell cultures established from acid sphingomyelinase (A-SMase) knock-out mice (Bianco et al., 2009. The authors therefore induced EAE in A-SMase−/− mice and found lower levels of microglia/macrophages MVs in their CSF relative to wt mice (FIG. 9C); this was associated to decreased CNS infiltration by inflammatory cells (FIG. 8C-D), inhibited disease development (FIG. 8E; FIG. 9A-B), and absence of tissue damage (FIG. 9D-E), further suggesting that shed MVs may have effector functions during EAE. Notably, the immunomodulator drug FTY720, effective in MS treatment, has been recently identified as an inhibitor of A-SMase by a mechanism similar to other tricyclic antidepressants and, consistent with our previous finding (Bianco et al., 2009), potently inhibits MP shedding (FIG. 13).

Figure 8:
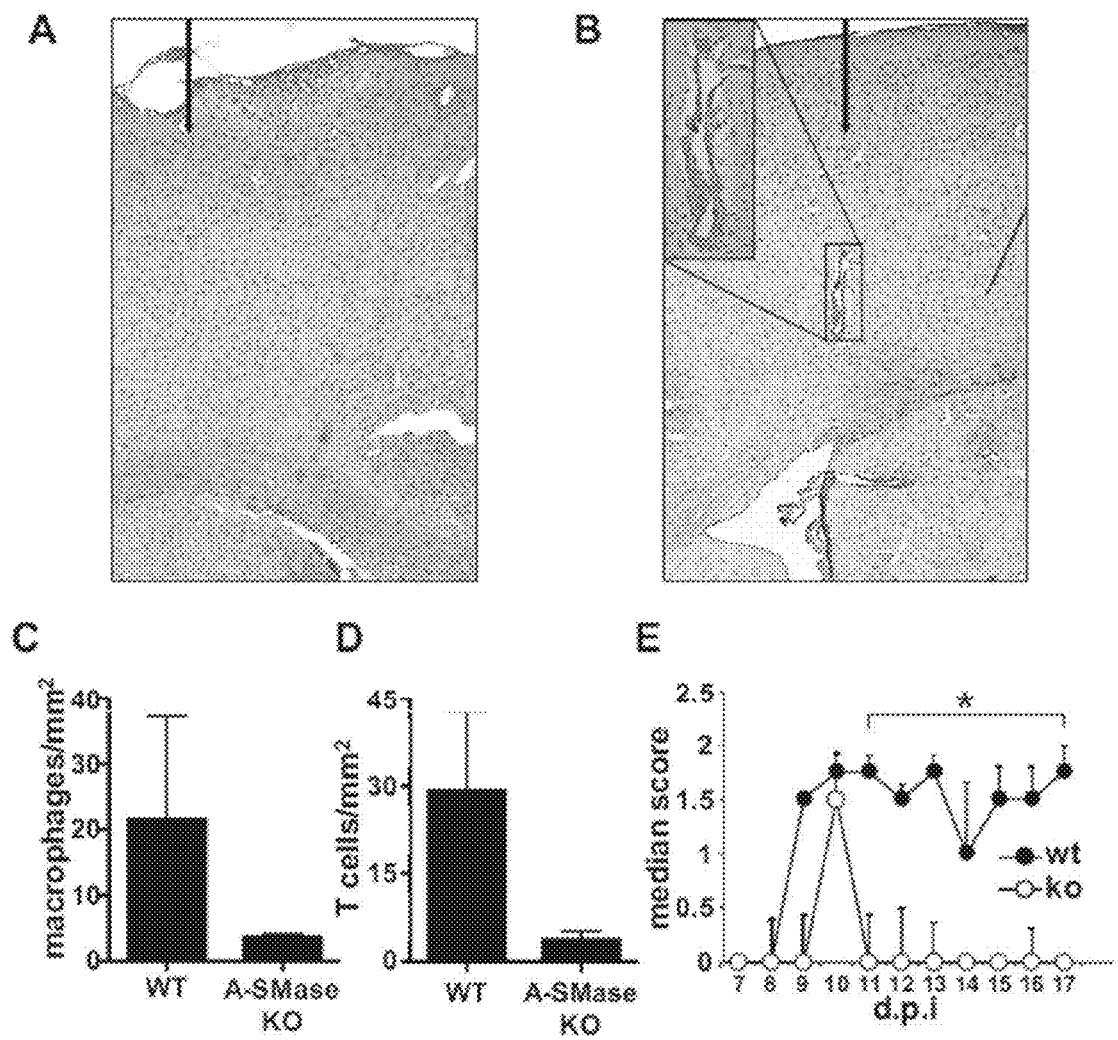
FIG. 8. Microglia/macrophage-derived MVs play an effector role during neuroinflammation in vivo. A-B. Coronal sections of the brain of EAE mice injected in the corpus callosum with saline or LPS-MVs. Hematoxylin and Eosin staining shows perivascular inflammatory cuffs along the needle trajectory (indicated by the arrows) only in mice injected with shed-MVs. Sections shown are representative of 5 saline-injected controls and 7 MVs injected mice. C-E. EAE induction in mice deficient for acid sphingomyelinase (A-SMase), impaired in MVs shedding (FIG. 9), results in reduced infiltration of the CNS by $IB4^+$ macrophages (C), and $CD3^+$ T cells (D), and in dramatically decreased disease severity (E) as compared to wild type (WT) littermates. n=5 mice per group. F. Quantitative analysis, by flow cytometry, of $IB4^+$ positive MVs in human CSF collected from patients with clinical isolated syndrome (CIS), the initial step of Multiple Sclerosis (MS), MS patients, and age and sex matched controls. G. We re-propose in form of a bar-graph on a linear scale, the mean values of controls and MS patients to show the significant difference that it is difficult to appreciate in F. (*$p<0.05$; **$p<0.01$; Mann-Whitney)
Figure 8:
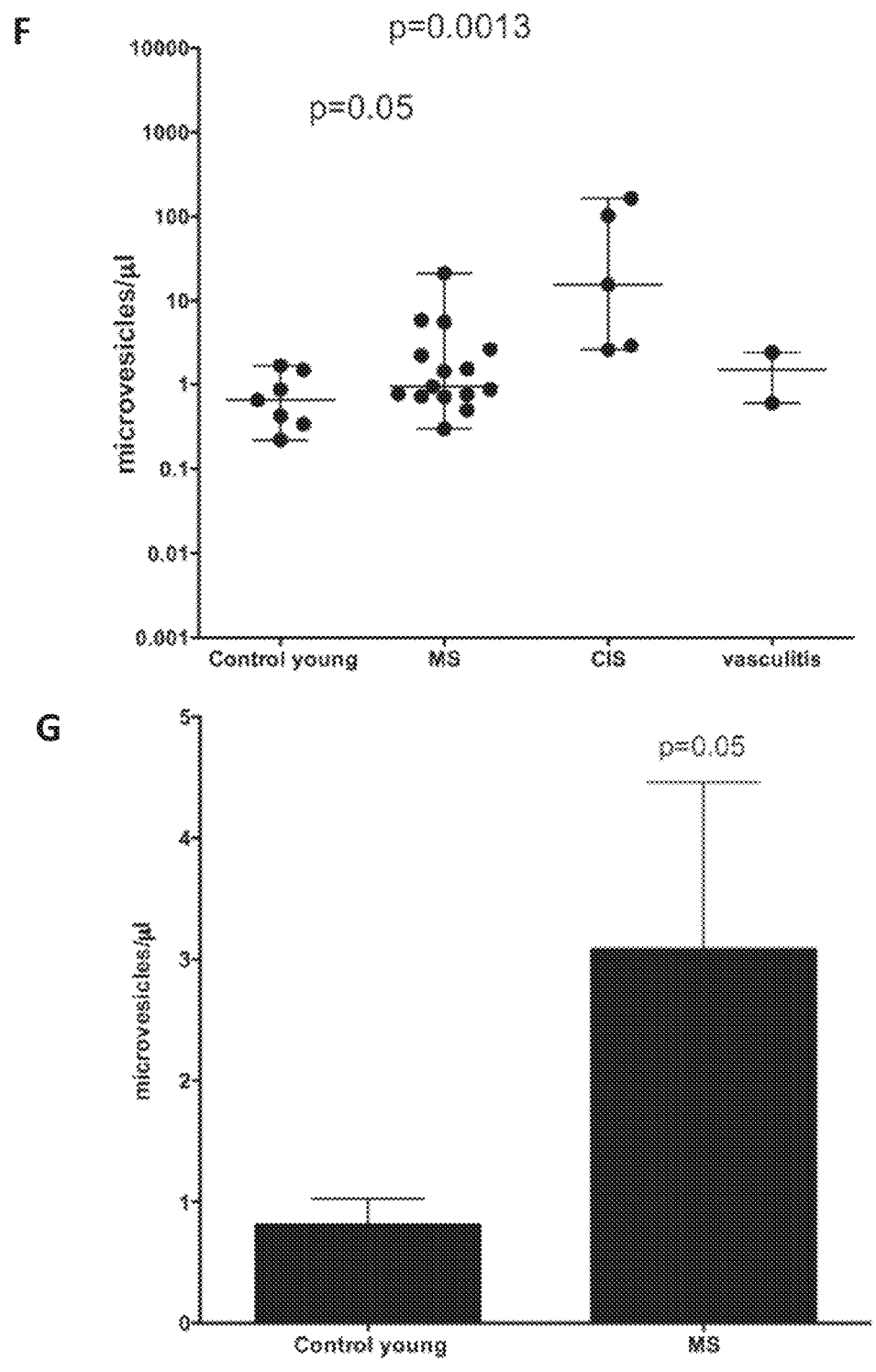

To verify if the amount of CSF MVs reflects microglia/macrophage activation in humans, the authors collected CSF from healthy donors, patients with Clinically Isolated Syndrome (CIS), considered an initial and acute stage of multiple sclerosis (MS), and patients with definite diagnosis of MS. Higher levels of microglia/macrophage MVs were detected in the CSF from CIS and MS patients, as compared to healthy controls (FIG. 8E). Notably, MVs isolated from CSF of MS patients propagate inflammation (data not shown).

As compared to young control subjects, patients affected by CIS had a significantly higher number of MVs/μl, as did patients with MS although at lower levels (FIG. 8F). It is tempting to speculate that in CIS, closer to an acute event, microglia is more activated and therefore levels are higher than in established MS patients, often undergoing lumbar puncture during a stable, remitting phase of the disease.

Since differences among controls and established MS patients are not easily appreciated on the logaritimic scale in FIG. 8F, young controls and MS patients are also shown on a linear scale and as bar graph (FIG. 8G). Mann-Whitney was used to test for statistical significance.

Figure 10:
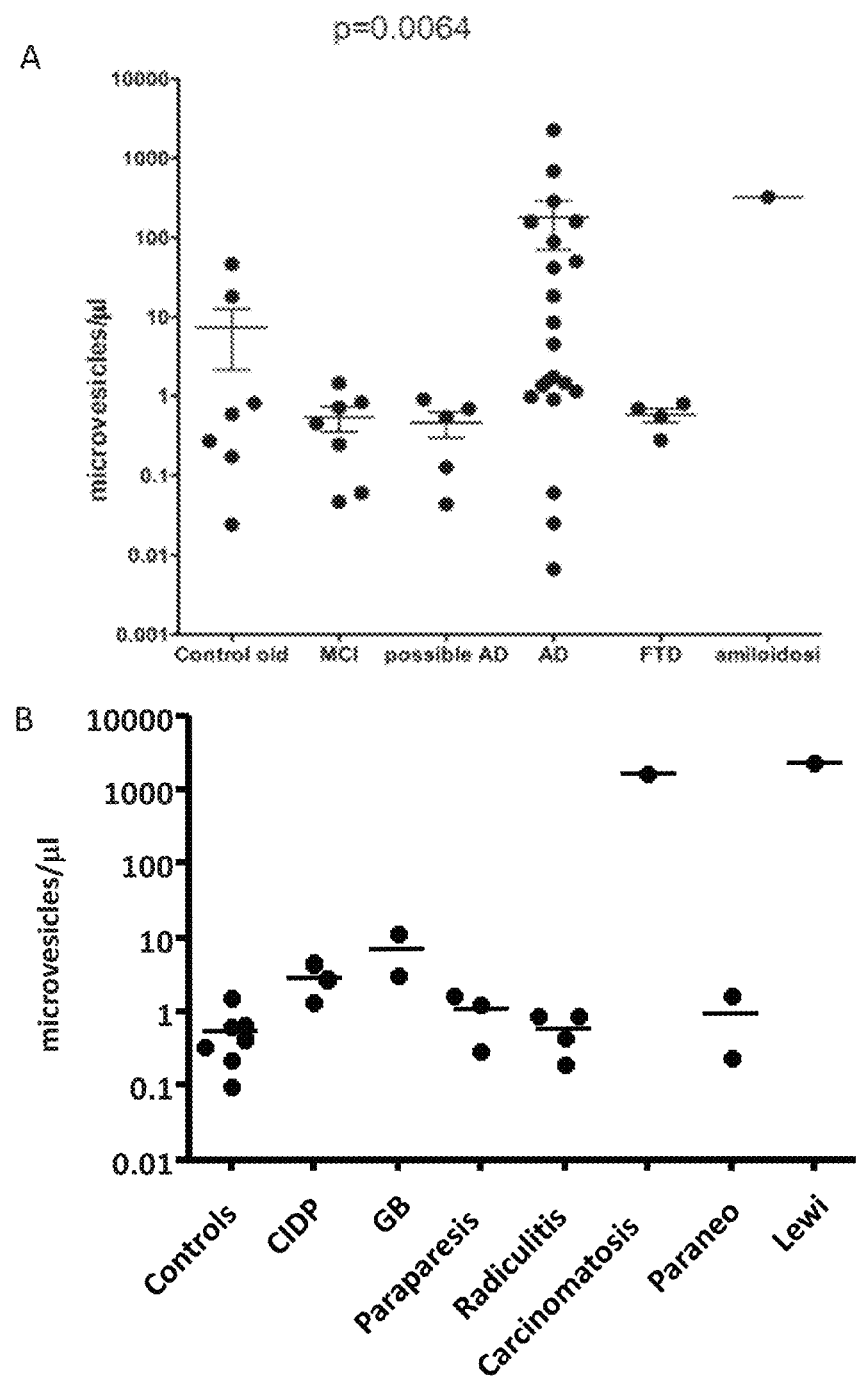
FIG. 10. Increased levels of myeloid microvesicles in AD patients. A-B. Quantitative analysis of total and IB4 positive microvesicle concentration in human CSF collected from patients with Mild Cognitive Impairment (MCI), Alzheimer Disease (AD), possible AD, Frtontotemporal Dementia (FTD), amyloidosis, Chronic Inflammatory Demyelinating Polyneuropathy (CIDP), Guillain-Barré Syndrome (GBS), paraparesis, radiculitis, meningeal carcinomatosis, paraneoplastic syndromes (paraneo), and Lewy body dementia (Lewy).

To determine whether the findings obtained with the EAE rodent models could be extended to human, the authors also collected CSF from patients affected by several neurological disorders including MS and Alzheimer's Disease (AD). The authors found that both total and myeloid MVs were significantly increased, as compared to healthy donors, in MS patients, but also in patients affected by inflammation of the peripheral nervous system (involving also spinal roots, close to the spinal cord, like Guillan-Barrè, CIDP, and radiculitis) (FIG. 10A,B). Furthermore, differently from other neurodegenerative disorders, also AD patients displayed a significant increase in total and myeloid MVs. These results indicate that myeloid MVs are readily detectable and increased in inflammatory and neurodegenerative disorders characterized by microglial activation.

As compared to older control subjects, only demented patients from AD group display a dramatically increased number of liquoral MVs, highly significant from a statistical point of view. Also in this case this finding is in agreement with knowledge that in AD microglia is widely activated in the brain while in other forms of dementia this phenomenon is limited (FIG. 11A).

With the exception of some outliers, most patients with other neurological disorders (amiloidosi, carcinomatosis, Lewis body) don't have increased MVs in the CSF. Only by collecting further samples of the same type, it can be ascertained if the outliers represent true positives in pathologies that have microglia activation (FIG. 10B).

Figure 11:
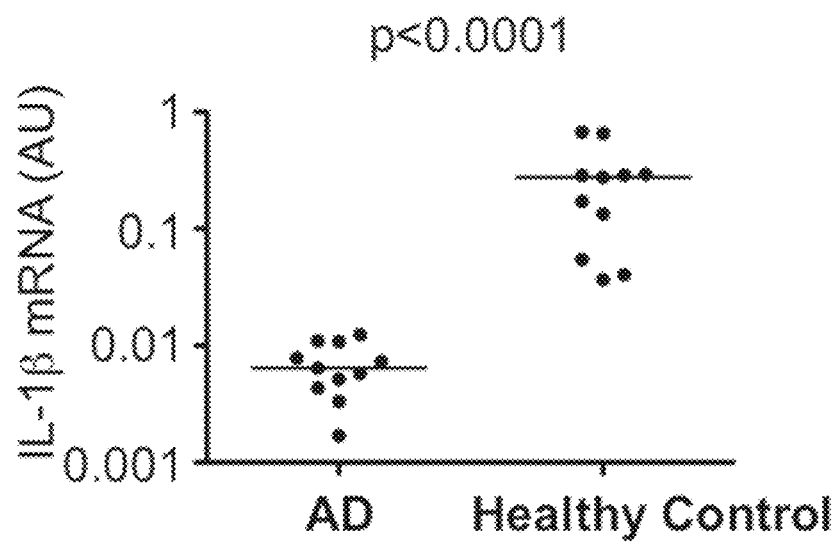
FIG. 11. MVs from AD patients display decreased content of IL-1beta mRNA. The authors isolated by ultracentrifugation MVs from the CSF of AD patients and controls. After RNA extraction we performed real-time RT-PCR to detect IL-1beta mRNA, and found a significant reduction in the MVs from AD patients.

On pelletted MVs obtained from the CSF of AD and control samples, the authors extracted RNA and performed real time RT-PCR for the detection of IL-1β mRNA using pre-developed assays by Applied Biosystems. Measures were normalized using 18s RNA. Surprisingly, AD patients showed a very significant decrease in IL-1β mRNA in their MVs, suggesting an anti-inflammatory phenotype of the microglia of origin, as also suggested by other evidence available in literature (FIG. 11).

In addition, the present data indicate that MVs shed from primary microglia do not significantly affect neuron viability in vitro, assessed up to 5 days after MV addition to hippocampal neurons (not shown).

Figure 12:
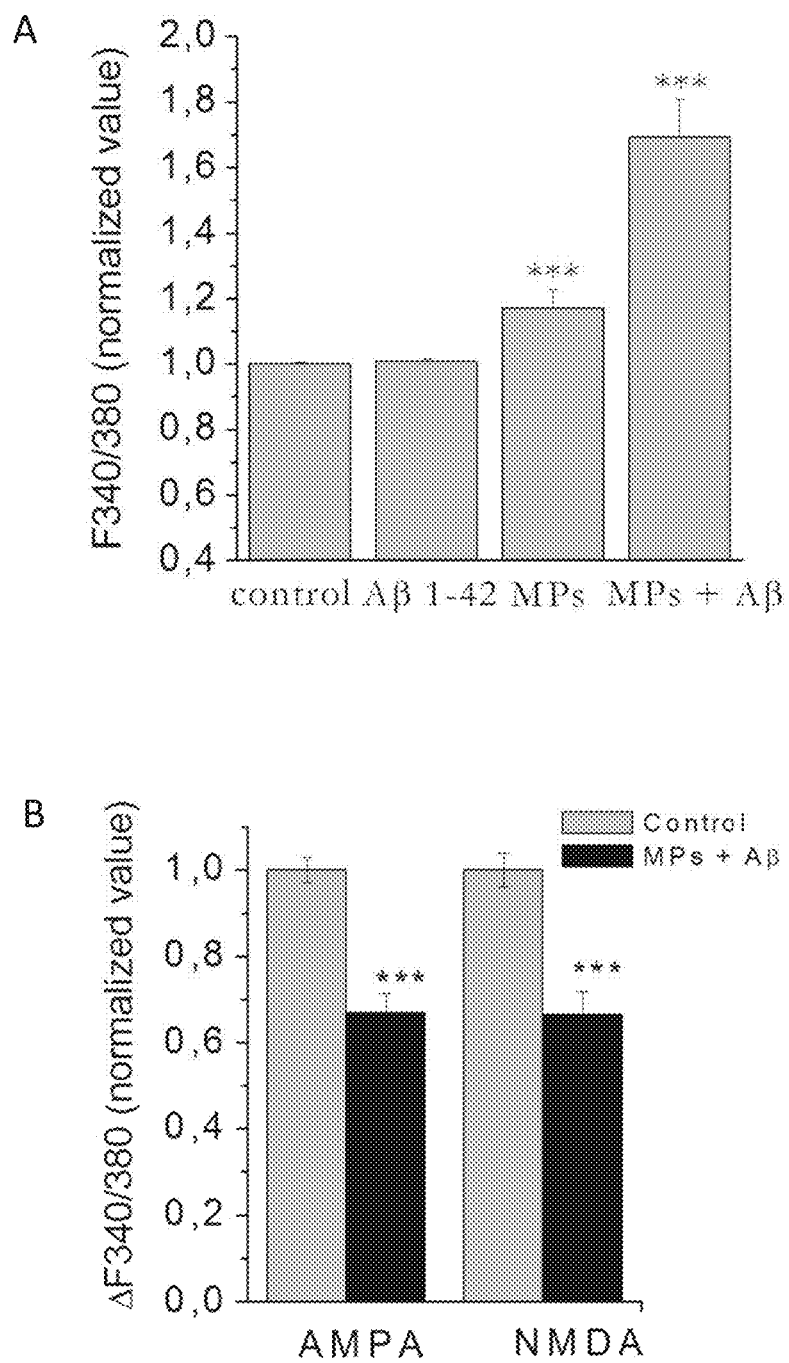
FIG. 12. Cultured hippocampal neurons were loaded with the ratiometric calcium dye FURA-2 for 1 h. During FURA-2 loading, neurons were exposed to microglia-derived microvesicles pre-incubated overnight in neuronal medium in the presence or in the absence of Abeta 1-42 (5 μM). Neurons were then wash in Kreb's ringer and resting calcium levels and calcium responsiveness to glutamate agonists (AMPA 100 μM, NMDA 100 μM) were evaluated using a single cell calcium imaging system. A: The histograms show basal cytosolic calcium concentration of control hippocampal neurons, neurons exposed to Abeta 1-42, pre-treated overnight in neuronal medium (Abeta), neurons exposed to MVs maintained overnight in neuronal medium (MVs) and neurons exposed to MVs maintained overnight in the presence of Abeta 1-42 in neuronal medium (MVs+Aβ). Note the high levels of basal calcium concentration in neurons exposed to Aβ-treated MVs. B: Histograms show the mean amplitude of calcium responses evoked by AMPA or NMDA in control neurons and neurons exposed to Aβ-treated MVs. 1 h exposure to Aβ-treated MVs significantly reduced neuronal responsiveness to glutamatergic agonists. C-E Neurons were exposed to Aβ-treated MVs for 1 h in the presence (E) or in the absence (D) of glutamatergic antagonists (20 μM CNQX and 100 μM APV), washed and maintained in culture medium for other 24 h, before being incubated with propidium iodide (PI) or annexin-V-FITC and fixed. PI uptake and fragmentation of neuronal cytoskeleton (C) and staining for annexin-V, quantified in F, indicate that Aβ-treated MVs strongly affect neuronal viability. Note that neuronal damage caused by Aβ-treated MVs is strongly prevented by glutamatergic antagonists. G The histograms show basal cytosolic calcium concentration of control neurons, neurons exposed to MVs pre-treated overnight with Abeta 1-42 in the absence or in the presence of glutamate antagonists. The presence of the glutamate antagonists APV and CNQX almost completely inhibited the increase in cytoplasmic calcium level induced by Aβ-treated MVs. H The histograms show basal cytosolic calcium concentration of control neurons and neurons exposed to CSF MVs isolated from a patient with AD, maintained overnight in the presence of Aβ in neuronal medium. I Quantitative analysis of mean amplitude of calcium responses evoked by AMPA or NMDA in control neurons and neurons exposed to Aβ-treated AD MVs.
Figure 12:
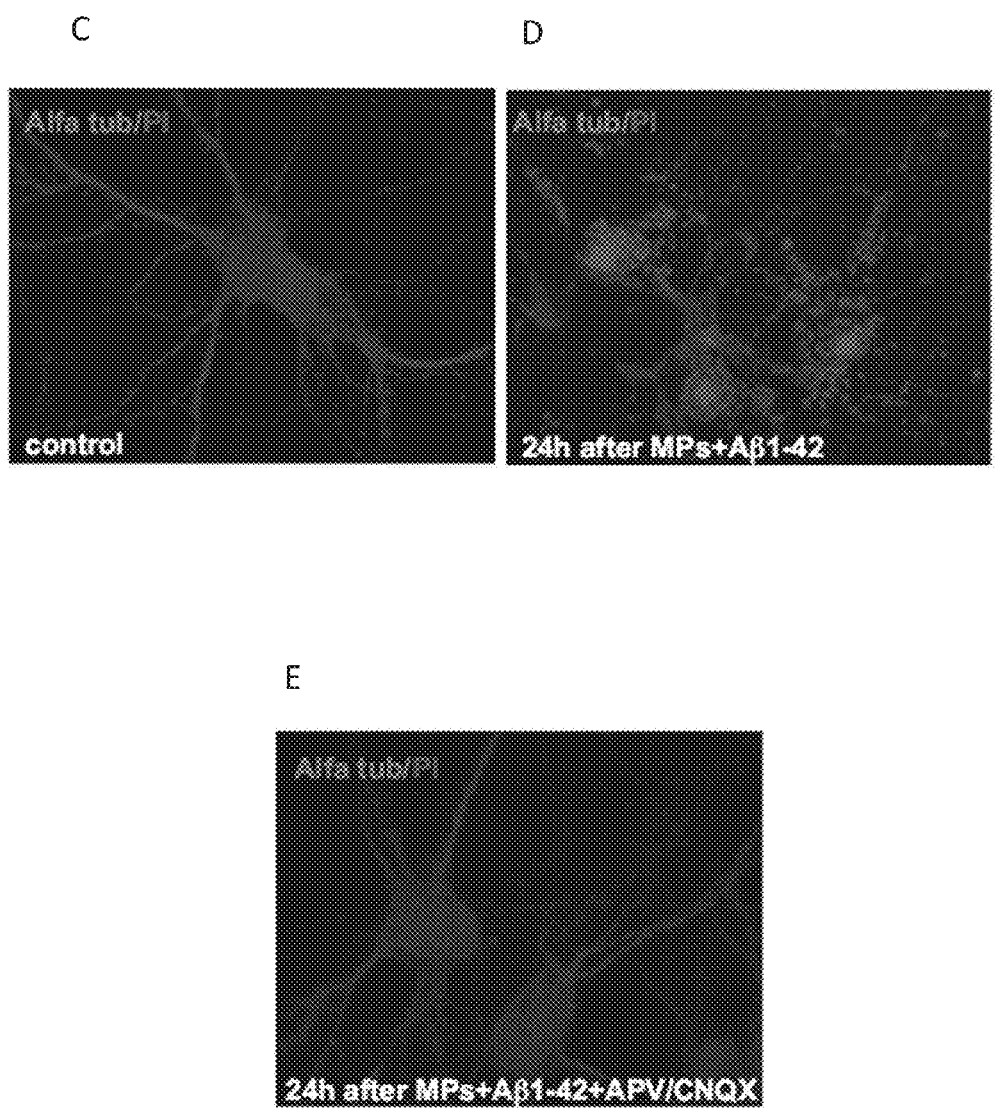
Figure 12:
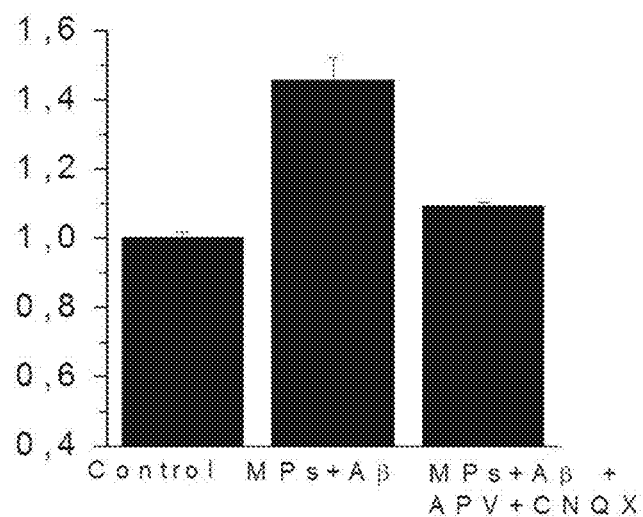
Figure 12:
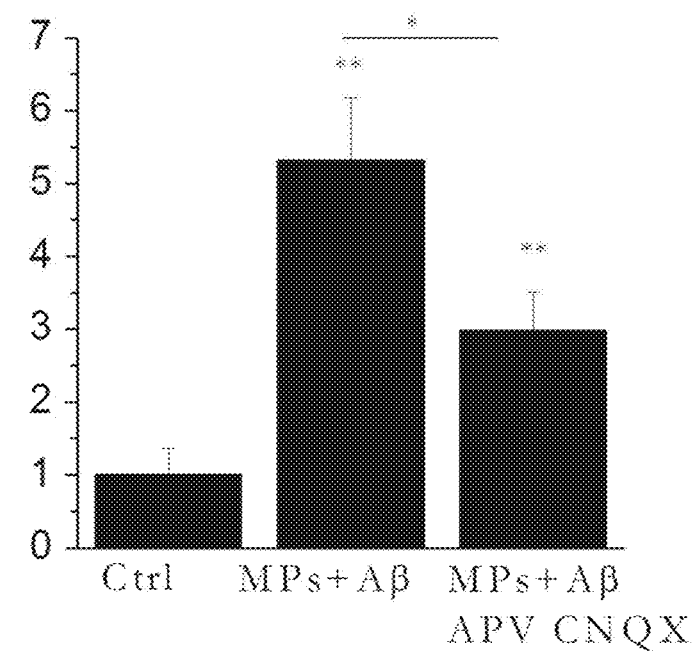
Figure 12:
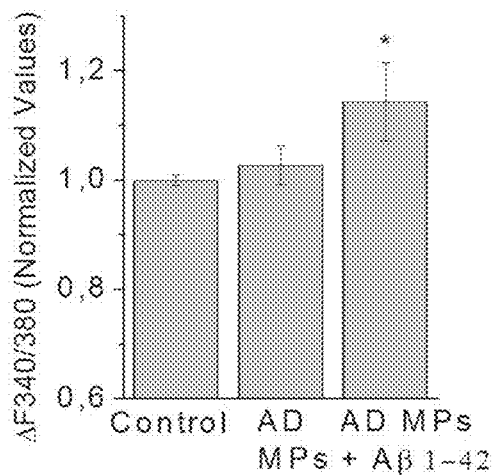
Figure 12:
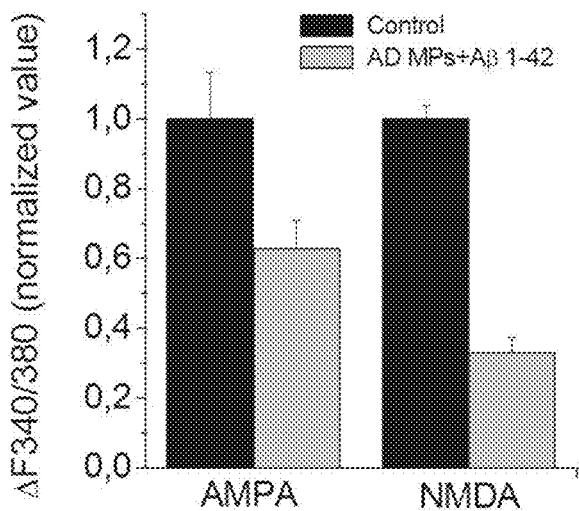

It has been recently shown that lipids such as sphingolipids and gangliosides disassemble amyloid fibrils, which are highly stable and biologically inert structures, into oligomers or other prefibrillar precursors, which are the main neurotoxic amyloid species (Martins et al., 2008). In addition, recent evidence indicated that amyloidogenic polypeptides can interact and penetrate into lipid bilayers of living cells as well as bilayers of artificial vesicles and promote vesicle leakage (Friedman and Caflisch, 2009). These observations opened the possibility that lipids, present in MV bilayer, can promote neurotoxicity of amyloidogenic peptides, and that amyloid polypeptides can favour MV disruption, inducing the release of neurotoxic compounds, like inflammatory cytokines, stored inside MVs. This hypothesis prompted the authors to investigate the effects of MVs pre-exposed to Aβ1-42 on cultured neurons (FIG. 12).

The authors found that 1 h exposure to MVs pre-incubated overnight with Aβ1-42 but not Aβ1-42 or MVs alone strongly affect the number of viable cultured neurons, as indicated by annexin-V staining (FIG. 12G) or propidium iodide (PI) uptake (FIG. 12C-E). Dendrites of neurons exposed to Aβ1-42-treated-MVs have a frequently fragmented or beaded appearance (FIG. 12D), display abnormal cytoplasmic calcium concentration (FIG. 12A) and reduced responsiveness to glutamate agonists (FIG. 12B). Interestingly, neuronal damage induced by Aβ1-42-treated MVs is strongly inhibited by glutamatergic antagonists (FIG. 12F-G), suggesting an excitotoxicity insult. Similar detrimental effects are induced in cultured neurons by MVs isolated from AD CSF, pre-incubated with Aβ1-42 (FIG. 12H-I). Finally, primary mouse microglia was pre-treated, or not, with FTY720, also named fingolimod or Gylenia (FIG. 13), currently in course of registration for the treatment of multiple sclerosis, for 18 h, then ATP was added for 30 min. to induce the release of Annex-inV$^+$ shed vesicles, as measured by FACS. Treatment with FTY720 completely prevented the release of shed vesicles above background levels. Since FTY720 is known to readily cross the blood brain barrier and to have effect also in the CNS of MS patients, these results may contribute to explain its beneficial activity in the CNS during neuroinflammation. Therefore, the number of shed vesicles in the CSF of treated patients represents a biomarker of therapeutic efficacy of MS or other neurological disorders therapeutic treatment.

It is then concluded that MVs of different origin can be detected in healthy CSF. The CSF is recipient of MVs carrying identity markers from all neural lineages, but myeloid MVs represent the major population. In addition, neuroinflammation enhances the release and modifies the content of myeloid MVs in the CSF.

Beside their pathogenic role, MVs produced by microglia leaking into the CSF represent a source of qualitative and quantitative information on microglia activation in vivo in humans, thus providing reliable biomarkers to diagnose and/or monitor the pathology course and the effectiveness of drugs targeting activated microglial cells.

REFERENCES

Al-Nedawi, K., et al. 2009. Cell Cycle 8, 2014-2018.
Ardoin, and Pisetsky 2008. Mod Rheumatol 18, 319-326.
Badovinac V, et al. J Neuroimmunol. 1998 May 1; 85(1):87-95.
Bianco, F., et al. 2005a. Brain Res Brain Res Rev 48, 144-156.
Bianco, F., et al. 2005b. J Immunol 174, 7268-7277.
Bianco F et al., EMBO J. 2009 28(8):1043-54
Calegari, F., et al. 1999. J Biol Chem 274, 22539-22547.
Cocucci, E., et al. 2009. Trends Cell Biol 19, 43-51.
Colton, C. A., et al. 2006 *J Neuroinflammation* 3, 27.
Diamant M et al., Eur J Clin Invest. 2004 June; 34(6):392-401. Review.
Distler J H et al., Arthritis Rheum. 2005 November; 52(11): 3337-48. Review.
Doeuvre, L., et al. J Neurochem 110, 457-468.
Emmanouilidou, E., et al. 2010 J Neurosci 30, 6838-6851.
Furlan R, et al. Gene Ther. 2007 January; 14(1):93-8. Epub 2006 Aug. 24.
Furlan R, et al. J Immunol. 1999 Sep. 1; 163(5):2403-9.
Hemmer B, et al. Nat Rev Neurosci. 2002 April; 3(4):291-301.
Horstman L L et al, Int Rev Neurobiol. 2007; 79:227-68.
Hunter M P, et al. PLoS ONE. 2008; 3(11):e3694. Epub 2008 Nov. 11.
Jung, S., et al. 2000 *Mol Cell Biol* 20, 4106-4114.
Kivisakk P et al., Ann Neurol. 2009 April; 65(4):457-69.

Leroyer A S et al., J Intern Med. 2008 May; 263(5):528-37. Review.

Mantovani, A., et al. 2004 *Trends Immunol* 25, 677-686.

Martin D, et al. J Neuroimmunol. 1995 September; 61(2): 241-5.

Michelucci, A., et al. 2009. *J Neuroimmunol* 210, 3-12 (2009).

Morel O et al., Curr Opin Hematol. 2004 May; 11(3):156-64. Review.

Morel O et al., Arterioscler Thromb Vasc Biol. 2006 December; 26(12):2594-604.

Pluchino, S., et al. 2008 *Brain* 131, 2564-2578.

Pollak Y, et al. J Neuroimmunol. 2003 April; 137(1-2):100-8.

Prineas J W, et al. Ann Neurol. 2001 November; 50(5):646-57.

Qu Y J, et al., Immunol. 2009 Apr. 15; 182(8):5052-62.

Ratajczak, J., et al. 2006. Leukemia 20, 1487-1495.

Rajendran et al., 2006 Proc Natl Acad Saci USA July 25; 103(30):11172-7.

Reboldi A et al., Nat Immunol. 2009 May; 10(5):514-23.

Scolding, N. J., et al. 1989. Nature 339, 620-622.

Simons M et al., Curr Opin Cell Biol. 2009 August; 21(4): 575-81.

Sriram S, et al. Neurology. 1997 February; 48(2):464-70. Review.

Takahashi J L, et al. Ann Neurol. 2003 May; 53(5):588-95.

Vella, L. J., et al. 2007. J Pathol 211, 582-590.

Wiemann B, et al. Exp Neurol. 1998 February; 149(2):455-63.

Zougman A, et al. J Proteome Res. 2008 January; 7(1):386-99. Epub 2007 Dec. 4.

---

The invention claimed is:

1. A method for diagnosing and/or monitoring of a neurological disease characterized by an inflammatory process wherein the neurological disease and/or the inflammatory process is characterized by microglial activation in a subject, the method comprising
  (a) labeling microglia/macrophage derived microvesicles with IB-4, wherein the microvesicles are present in a cerebrospinal fluid sample obtained from the subject;
  (b) measuring the amount of said labelled myeloid microglia/macrophage derived microvesicles in said sample obtained from the subject,
wherein if the measured amount is above a control value, the subject is affected by a neurological disease characterized by an inflammatory process.

2. The method according to claim 1, wherein the microglia/macrophage derived microvesicles are further positive for a marker selected from the group consisting of Iba-1, OX42 and CD11b.

3. The method according to claim 1 wherein the amount of the microglia/macrophage derived microvesicles is measured by means of flow cytometry technology.

4. The method according to claim 1 wherein the amount of the microglia/macrophage derived microvesicles is measured by means of immunogold electron microscopy.

5. The method according to claim 1 wherein the control value is between 1.5 to 2 microvesicles/µl.

6. A method for predicting and/or monitoring the efficacy of a treatment or progression of a neurological disease, wherein the neurological disease is characterized by an inflammatory process in a subject, comprising:
  (a) labeling microglia/macrophage derived microvesicles with IB-4, wherein the microvesicles are present in a cerebrospinal fluid sample obtained from the subject,
  (b) measuring the amount of the labeled microglia/macrophage derived microvesicles in a cerebrospinal fluid sample obtained from the subject, and
  (c) comparing the measured amount to a control value.

7. The method according to claim 6 wherein the neurological disease is characterized by an inflammatory process.

8. The method according to claim 7 wherein the neurological disease and/or the inflammatory process is characterized by microglial activation.

9. The method according to claim 6 wherein the neurological disease is selected from the group consisting of Multiple sclerosis, Alzheimer's disease, clinically isolated syndrome (CIS), Guillain-Barré Syndrome (GBS), neuromyelitis optica (NMO), chronic inflammatory demyelinating polyneuropathy (CIDP), frontotemporal dementia, radiculitis, encephalitis and meningoencephalitis.

10. The method according to claim 6, wherein the microglia/macrophage derived microvesicles are further positive for a marker selected from the group consisting of Iba-1, and OX42.

11. The method according to claim 6, wherein the amount of the microglia/macrophage derived microvesicles is measured by means of flow cytometry technology.

12. The method according to claim 6, wherein the amount of the microglia/macrophage derived microvesicles is measured by means of immunogold electron microscopy.

* * * * *